(12) United States Patent
Blurton et al.

(10) Patent No.: US 11,497,640 B1
(45) Date of Patent: Nov. 15, 2022

(54) PERIANAL SUPPORT DEVICE WITH FLEXIBLE SIDE SUPPORTS

(71) Applicant: Stetrix, Inc., Bartlett, TN (US)

(72) Inventors: David D. Blurton, Whiteville, TN (US); Mark Buchanan, Atoka, TN (US)

(73) Assignee: Stetrix, Inc., Bartlett, TN (US)

( * ) Notice: Subject to any disclaimer, the term of this patent is extended or adjusted under 35 U.S.C. 154(b) by 0 days.

(21) Appl. No.: 17/578,951

(22) Filed: Jan. 19, 2022

Related U.S. Application Data

(63) Continuation of application No. 17/512,244, filed on Oct. 27, 2021.

(51) Int. Cl.
*A61F 5/00* (2006.01)

(52) U.S. Cl.
CPC .................................. *A61F 5/0093* (2013.01)

(58) Field of Classification Search
CPC ....... A61F 5/0093; A61B 17/42; A61M 29/00
See application file for complete search history.

(56) References Cited

U.S. PATENT DOCUMENTS

| | | |
|---|---|---|
| 1,511 A | 3/1840 | Truss |
| 316,903 A | 4/1885 | Lytle |
| 453,880 A | 6/1891 | Coffee |
| 942,590 A | 12/1909 | Sanborn |
| 969,134 A | 8/1910 | Cowie |
| 1,249,195 A | 12/1917 | Raines |
| 1,547,127 A | 7/1925 | Metzger |
| 1,711,294 A | 4/1929 | Weitzner |
| 1,877,766 A | 9/1932 | Kennedy |

(Continued)

FOREIGN PATENT DOCUMENTS

| | | |
|---|---|---|
| GB | 233980 | 5/1925 |
| GB | 512161 | 8/1939 |

(Continued)

OTHER PUBLICATIONS

Abramowitz et al., "Epidemiology of anal lesions (fissure and thrombosed external hemorroid) during pregnancy and post-partum", Gynecol Obstet Fertil 2003, No. 31, 546-549, 4 pages.

(Continued)

*Primary Examiner* — Camtu T Nguyen
(74) *Attorney, Agent, or Firm* — Haynes and Boone, LLP

(57) ABSTRACT

A perianal support device includes a central support element with an apex having a continuous contact surface along the apex to interface with a patient's perianal tissue. Compression elements extend laterally away from each apex side of the central support element. Each compression element may have a narrower proximal end to the central support element and a wider distal end, and be flexible to bend to the gluteal cleft anatomy. The surface of each compression element that faces the patient in use may be covered, at least partially, with a loop material on the wider distal end. Each compression element may also have the opposite surface covered, at least partially, with foam. The central support element and compression elements may be integrally formed. A gripping tab is also provided at a distal end of each compression element, providing an easy location for medical staff to grasp for placement and removal.

20 Claims, 8 Drawing Sheets

(56) References Cited

U.S. PATENT DOCUMENTS

| | | |
|---|---|---|
| 2,128,670 A | 8/1938 | Bolder |
| 2,468,348 A | 4/1949 | Shore |
| 2,653,599 A | 9/1953 | Bell |
| 2,672,862 A | 3/1954 | Krauss |
| 2,779,330 A | 1/1957 | Reid |
| 3,712,300 A | 1/1973 | Davidowitz |
| 3,826,242 A | 7/1974 | Eggers |
| 3,939,842 A | 2/1976 | Harris |
| 3,985,125 A | 10/1976 | Rose |
| 4,240,436 A | 12/1980 | Singleton |
| 4,263,914 A | 4/1981 | Pawlak |
| 4,365,631 A | 12/1982 | Kline |
| 4,421,504 A | 12/1983 | Kline |
| 4,432,351 A | 2/1984 | Hoary |
| 4,439,180 A | 3/1984 | Kline |
| 4,445,898 A | 5/1984 | Jensen |
| 4,445,899 A | 5/1984 | Bond |
| 4,484,919 A | 11/1984 | Sohn et al. |
| 4,520,807 A | 6/1985 | Rotter |
| 4,583,542 A | 4/1986 | Boyd |
| 4,638,806 A | 1/1987 | Bartlett |
| 4,670,419 A | 6/1987 | Uda et al. |
| 4,686,966 A | 8/1987 | Tsai |
| 4,891,847 A | 1/1990 | Baker et al. |
| 4,966,130 A | 10/1990 | Montaldi |
| 5,072,720 A | 12/1991 | Francis et al. |
| 5,178,627 A | 1/1993 | Hudock |
| 5,179,937 A | 1/1993 | Lee |
| 5,231,973 A | 8/1993 | Dickie |
| 5,263,926 A | 11/1993 | Wilk |
| 5,377,667 A | 1/1995 | Patton et al. |
| 5,509,893 A | 4/1996 | Pracas |
| 5,676,637 A | 10/1997 | Lee |
| 5,695,484 A * | 12/1997 | Cox ............... A61F 2/0009 604/304 |
| 5,704,894 A | 1/1998 | Boutos |
| 5,800,485 A | 9/1998 | Trop et al. |
| 5,891,074 A | 4/1999 | Cesarczyk |
| 5,908,379 A | 6/1999 | Schaefer et al. |
| 5,924,423 A | 7/1999 | Majlessi |
| 5,935,595 A | 8/1999 | Steen |
| 5,985,395 A | 11/1999 | Comstock et al. |
| 6,083,241 A | 7/2000 | Longo et al. |
| 6,102,271 A | 8/2000 | Longo et al. |
| 6,142,933 A | 11/2000 | Longo et al. |
| D437,642 S | 2/2001 | Caballero |
| 6,364,852 B1 | 4/2002 | Lee |
| 6,428,004 B1 | 8/2002 | McQuitty et al. |
| 6,503,192 B1 | 1/2003 | Ouchi |
| 6,517,562 B1 | 2/2003 | Holland |
| 6,537,132 B1 | 3/2003 | Alberts |
| 6,627,632 B2 | 9/2003 | Parks et al. |
| 6,712,841 B2 | 3/2004 | Gomez |
| 6,716,229 B2 | 4/2004 | Toth |
| 6,742,522 B1 | 6/2004 | Baker et al. |
| 6,913,573 B1 | 7/2005 | Viscomi et al. |
| 6,916,494 B2 | 7/2005 | Park |
| 6,916,967 B2 | 7/2005 | Wright et al. |
| 6,991,813 B2 | 1/2006 | Xu |
| 7,048,706 B2 | 5/2006 | Cea |
| 7,135,606 B1 | 11/2006 | Dozier et al. |
| 7,160,294 B2 | 1/2007 | Croft |
| 7,309,809 B2 | 12/2007 | Smith et al. |
| 7,354,446 B2 | 4/2008 | Lebner |
| 7,673,633 B2 | 3/2010 | Blurton et al. |
| 7,766,931 B2 | 8/2010 | Blurton |
| 8,062,277 B2 | 11/2011 | Fleming |
| 8,066,009 B2 | 11/2011 | Blurton |
| 8,123,760 B2 | 2/2012 | Blurton |
| 8,277,427 B2 | 10/2012 | Edvardsen et al. |
| 8,353,884 B2 | 1/2013 | Hansen et al. |
| 2001/0000731 A1 | 5/2001 | Jia et al. |
| 2001/0003157 A1 | 6/2001 | Toth |
| 2002/0072522 A1 | 6/2002 | Parks et al. |
| 2002/0142902 A1 | 10/2002 | Stein |
| 2002/0147482 A1 | 10/2002 | Carter |
| 2002/0187990 A1 | 12/2002 | Parks et al. |
| 2002/0192273 A1 | 12/2002 | Buseman et al. |
| 2003/0021850 A1 | 1/2003 | Xu |
| 2003/0229263 A1 | 12/2003 | Connors et al. |
| 2003/0236442 A1 | 12/2003 | Connors et al. |
| 2004/0076688 A1 | 4/2004 | Park |
| 2004/0088031 A1 | 5/2004 | Gomez |
| 2004/0217146 A1 | 11/2004 | Beck |
| 2004/0254590 A1 | 12/2004 | Hoffman et al. |
| 2005/0000003 A1 | 1/2005 | Bushelman |
| 2005/0049660 A1 | 3/2005 | Croft |
| 2005/0214327 A1 | 9/2005 | Brooks et al. |
| 2005/0283050 A1 | 12/2005 | Gundlapalli et al. |
| 2006/0025766 A1 | 2/2006 | Heinrich et al. |
| 2006/0144897 A1 | 7/2006 | Jankowski et al. |
| 2006/0153927 A1 | 7/2006 | Xu |
| 2006/0155340 A1 | 7/2006 | Schuler et al. |
| 2006/0195146 A1 | 8/2006 | Tracey et al. |
| 2006/0195153 A1 | 8/2006 | DiUbaldi et al. |
| 2006/0198883 A1 | 9/2006 | Parks et al. |
| 2007/0011802 A1 | 1/2007 | Holland |
| 2007/0053957 A1 | 3/2007 | Kennedy et al. |
| 2008/0097472 A1 | 4/2008 | Agmon et al. |
| 2009/0043169 A1* | 2/2009 | Trieu ............... A61B 17/42 600/220 |
| 2009/0148503 A1 | 6/2009 | Trieu |

FOREIGN PATENT DOCUMENTS

| | | |
|---|---|---|
| GB | 1127548 A | 9/1968 |
| JP | 7-275309 | 10/1995 |
| JP | 2001-129004 | 5/2001 |
| JP | 2001170093 | 6/2001 |
| WO | WO02-13680 A2 | 2/2002 |
| WO | WO03-053255 A1 | 7/2003 |
| WO | WO 2007/019095 | 2/2007 |

OTHER PUBLICATIONS

Danel, "Magnitude of Maternal Morbidity During Labor and Delivery: United States, 1993-1997", American Journal of Public Health, Apr. 2003, vol. 93, No. 4, , pp. 631-634, 4 pages.

Masahiro Takana, Anal Diseases, Pregnancy and Parturition, 1990, Nippon Daicho Komonbyo Gakkai Zasshi, Tokyo, 1990; 43(6); pp. 1077-1082; with English translation, 64 pages.

Frederick Francis Burghard, various authors, "A System of Operative Surgery, vol. IV (of 4)," Dec. 26, 2012 [Ebook #41710] , www.gutenberg.org, 17 pages.

* cited by examiner

PERIANAL SUPPORT DEVICE WITH FLEXIBLE SIDE SUPPORTS

PRIORITY

This application is a continuation of U.S. Ser. No. 17/512,244 filed on Oct. 27, 2021, which is incorporated herein by reference in its entirety.

TECHNICAL FIELD

This disclosure relates in general to devices and methods for inhibiting perianal tissue damage. More particularly, in some implementations, this disclosure relates to a perianal support device that provides compression at an apex of the perianal support device while providing flexible side supports that conform generally to the buttocks of the patient when applied, and methods of applying during childbirth labor.

INTRODUCTION

A typical labor process during childbirth begins with the onset of rhythmic uterine contractions and ends with complete cervical dilatation. The labor progress is generally driven by two types of labor forces. The primary force is produced by the involuntary contractions of the mother's uterus (i.e., uterine muscle contractions). The secondary force is produced by the increase of intra-abdominal pressure created by voluntary contractions of the mother's abdominal muscles, including pelvic musculatures and diaphragm. These forces act synergistically to increase the intrauterine pressure and aid the expulsion of the child from the uterus.

Using epidurals and pain relieving drugs during the labor and delivery process can desensitize the birthing mother from experiencing the natural body signals needed to push the baby through the birth canal and, thereby, ultimately delay the progression of childbirth. One indication of this phenomenon is that in recent years, there has been a dramatic increase in the incidence of children born by Cesarean childbirth, which can significantly increase the cost to the healthcare system when compared to a natural vaginal delivery. In addition, the recovery from a Cesarean operation may take significantly more time compared to a natural vaginal child delivery. These factors can lead to the weakening of the secondary force, and sequentially to delayed labor duration or even dystocia (arrest of labor). In some instances, therefore, the ineffective or inadequate pushing by the mother can delay the duration of labor, which can lead to injuries of the pelvic floor, fetal distress, higher rate of infant mortality, neonatal seizures, postpartum hemorrhage, and/or to delivery by Cesarean section.

While prior apparatus and methods like those disclosed in U.S. Pat. Nos. 8,123,760 and 7,673,633 provide stable support for the soft perianal tissues near the anal orifice, these can be further improved to provide additional benefits for labor management to increase intrauterine pressure (e.g., by strengthening contractions and pushing), thereby decreasing the duration of the second stage of labor and/or decreasing the incidence of Cesarean childbirth. More specifically, there exists a need for devices that conform to the contours of the patient's buttocks when applied to supply compression to an apex supporting the perianal tissues, thereby avoiding situations where contact between the apex and perianal tissue is lost due to the secondary force. This may promote more effective fetal descent, thereby decreasing the duration of the second stage of labor and increasing the likelihood of successful vaginal births as well as to suppress the development of hemorrhoids.

SUMMARY

According to some aspects of the present disclosure, a perianal support device may include a central support element comprising a continuous compression surface apex dimensioned to extend across an anal orifice of a patient in a sagittal plane of the patient. The perianal support device may also include a first compression element extending from the central support element in a first lateral direction, the first compression element comprising a first resilient, flexible member configured to follow a first contour of a first buttock of the patient, the first compression element further comprising a first surface comprising a first loop portion of a hook and loop fastener facing the first buttock of the patient, and a second surface comprising a soft material facing away from the first buttock. The first loop portion is configured to releasably attach to a first hook portion of the hook and loop fastener of a first anchor pad releasably attached across a first crown of the first buttock. The perianal support device may also include a second compression element extending from the central support element in a second lateral direction opposite the first lateral direction, the second compression element comprising a second resilient, flexible member configured to follow a second contour of a second buttock of the patient, the second compression element further comprising a third surface comprising a second loop portion of the hook and loop fastener facing the second buttock of the patient, and a fourth surface comprising the soft material facing away from the second buttock. The second loop portion is configured to releasably attach to a second hook portion of the hook and loop fastener of a second anchor pad releasably attached across a second crown of the second buttock. The perianal support device may also include a first tab comprising a third hook portion of the hook and loop fastener configured to releasably attach to the first surface at a first distal end of the first compression element, and a second tab comprising a fourth hook portion of the hook and loop fastener configured to releasably attach to the third surface at a second distal end of the second compression element. The first tab is configured for gripping to manually attach the first surface to the first anchor pad and the second tab is configured for gripping to manually attach the third surface to the second anchor pad.

According to some aspects of the present disclosure, a perianal support device may include a central support element comprising a continuous compression surface apex dimensioned to extend across an anal orifice of the patient in a sagittal plane of the patient. The perianal support device may also include a first compression element comprising a first resilient, flexible member configured to follow a first contour of a first buttock of the patient and a first surface facing the first buttock of the patient, the first surface having a first lateral extent configured to releasably attach to a first anchor pad placed across a first crown of the first buttock, the first compression element further comprising a first tab extending outwardly laterally from said first compression element, said first tab having a first lateral tab extent less than the first lateral extent. The perianal support device may also include a second compression element comprising a second resilient, flexible member configured to follow a second contour of a second buttock of the patient and a second surface facing the second buttock of the patient, the second surface having a second lateral extent configured to releasably attach to a second anchor pad placed across a second crown of the second buttock, the second compression element further comprising a second tab extending outwardly from said second compression element, said second tab having a second lateral extent less than the second lateral extent. The first and second tabs may be configured for gripping to manually attach the first and second surfaces to the first and second anchor pads, respectively.

According to some aspects of the present disclosure, a perianal support device for use on a patient may include a central contact surface dimensioned to extend across an anal orifice of the patient in a sagittal plane of the patient from an anterior portion posterior to a vaginal opening of the patient to a posterior portion posterior to the anal orifice of the patient. The perianal support device may also include a first compression element extending from the central contact surface in a first lateral direction, the first compression element comprising a first surface configured to follow a first contour of a first buttock of the patient within a gluteal cleft of the patient, and releasably attach to a first anchor pad placed across a first crown of the first buttock. The perianal support device may also include a second compression element extending from the central contact surface in a first lateral direction, the second compression element comprising a second surface configured to follow a second contour of a second buttock of the patient within the gluteal cleft of the patient, and releasably attach to a second anchor pad placed across a second crown of the second buttock. The support device comprises a resilient, flexible member comprising a thin plastic substrate extending continuously from the first distal end of the first compression element, across the central support element, to the second distal end of the second compression element, the first surface and the second surface being disposed on one side of the thin plastic substrate separated by the central contact surface, and a medical grade foam being disposed on an opposite side of the thin plastic substrate continuously from the first distal end of the first compression element, across the central support element to the second distal end of the second compression element.

Further objects, forms, implementations, aspects, features, benefits, and advantages of the present disclosure shall become apparent from the detailed drawings and descriptions provided herein.

DETAILED DESCRIPTION

Figure 1A:
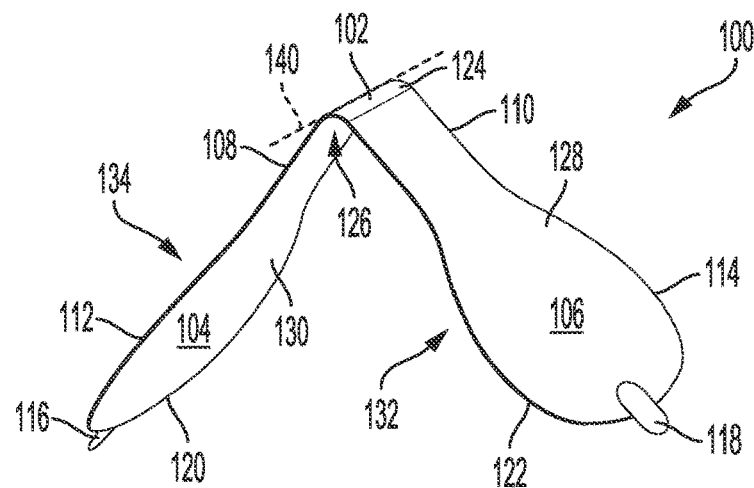
FIG. 1A is a perspective view of a perianal support apparatus according to aspects of the present disclosure.

For the purposes of promoting an understanding of the principles of the present disclosure, reference will now be made to certain implementations, or examples, illustrated in the drawings and specific language will be used to describe the same. It will nevertheless be understood that no limitation of the scope of the present disclosure is thereby intended. Any alterations and further modifications in the described implementations, and any further applications of the principles of the present disclosure as described herein are contemplated as would normally occur to one skilled in the art to which the present disclosure relates.

The present disclosure is directed to perianal support devices and methods of using the same to inhibit or prevent perianal tissue damage, such as during childbirth labor. The perianal support device provides compression at an apex of the perianal support device while providing flexible side supports that conform generally to the buttocks of the patient when applied. Specifically, the perianal support device may include a central support element that includes the apex and a contact surface extending along the apex to provide a soft interface between the device and the patient's perianal tissue (and, in some examples, to also provide absorbency for fluids in the proximity).

A compression element may extend laterally away from each side of the central support element. Each compression element may have a narrower proximal end (proximal to the central support element) and a wider distal end. The wider distal end of each central support element may provide a larger surface area with which the respective compression element may connect to a region approximately at the crown of each buttock of the patient. Each compression element may be flexible enough to bend as it extends away from the central support element. The bending may be to conform to the anatomy of the patient extending out of the gluteal cleft. Further, each compression element may have a surface facing the patient that is covered, at least partially, with a loop material (or other type of adhering member). This may be located on the wider distal end. Each compression element may also have the opposite surface (facing away from the patient) that is covered, at least partially, with a softer material, such as a medical grade foam. Finally, the central support element and both compression elements may be integrally formed together, sharing at least a common substrate (e.g., a medical grade polycarbonate).

The perianal support device may further include a gripping portion, or tab, at a distal end of each compression element. The tabs may be formed from a hook material such that they may easily engage with the loop material covering at least the distal ends of the compression elements. There may be a tab for the distal end of each compression element (or multiple tabs may be placed/used on each compression element). The tab may be included to provide an easy location for a user to grasp. For example, a physician may use the tab to grasp to easily place the distal portions of each compression element onto a receiving anchor pad at the crown of each buttock, and/or to easily grasp and pull to quickly detach and remove the perianal support device from the patient. In some other examples, the tabs may also be integrally formed with the compression elements (or one or more layers of the compression elements) as well.

In some aspects, the devices and systems described herein may cover all or most of the anal orifice of the patient when applied (e.g., the central support element's apex extending across the anal orifice), and thereby suppress defecation, hemorrhoid development, and/or the advancement of existing hemorrhoids during childbirth labor. In some instances, the embodiments disclosed herein enhance the willingness of the patient to push when instructed by lessening the patient's fear of trauma and/or involuntary defecation as a result of pushing. Yet further, the perianal support device may provide a tactile sensation to patient, often even after administration of an epidural and may provide a pushing focal point to enhance the effectiveness of contractions. For example, when placed on a patient the perianal support device may apply sufficient pressure to the perianal region to stimulate the patient's physiologic urge to push (e.g., similar to the Ferguson reflex, which triggers uterine contractions). These effects may result in a shortening of the second stage of labor by enhancing the effectiveness of contractions (e.g., by increasing the intensity and or number of contractions) in advancing the baby down the birth canal.

The perianal support device disclosed herein may efficiently, effectively, removably, and safely prevent prolonged duration of labor and dystocia due to various causes, including, without limitation, systemic analgesia, epidural anesthesia, and/or maternal exhaustion, which may avoid a Cesarean section and/or an instrument-assisted delivery. Given that weakening of the secondary labor force has been reported in patients receiving epidural anesthesia, use of the perianal support device may effectively enable a safer and less painful delivery under anesthesia by preventing weakening of the secondary labor force (e.g., even under anesthesia). Thus, the perianal support device may reduce the necessity of Cesarean section deliveries and/or instrument-assisted deliveries by guiding the patient with respect to the strength and focus of contractions to generate a more effective pushing effect on the baby. By reinforcing the secondary labor force, the labor assistance systems disclosed herein may lower the dosage of oxytocin (or other pharmacological contraction aides) necessary during labor. In some instances, the systems disclosed herein may be used to cooperatively complement the effects of oxytocin during labor. Use may further provide a reduction in the incidence of defecation, hemorrhoid development, and/or the advancement of existing hemorrhoids during childbirth labor.

Aspects of the present disclosure achieve these and other benefits by the perianal support device which improves upon prior approaches by making the compression elements that extend away from the central support element flexible relative to the central support element (and relative to prior approaches). Thus, the compression elements may conform to the anatomy of the patient's gluteal cleft (e.g., bending over the curvature of the buttocks to rest on the crowns of each buttock). The compression elements may further be releasably engaged with anchor pads on the general region of the crown of each buttock, instead of requiring additional straps that attach to and extend away from rigid compression elements of prior approaches. This may provide a more secure and stable pressure engagement during contractions (voluntary or involuntary).

Figure 1B:
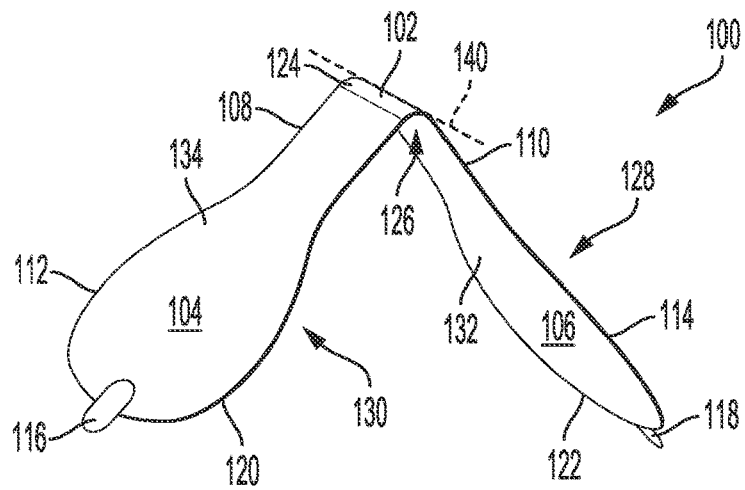
FIG. 1B is a perspective view of a perianal support apparatus, opposite to the view of FIG. 1A, according to aspects of the present disclosure.

Illustrated in FIGS. 1A-1G are different views of a perianal support apparatus 100 according to aspects of the present disclosure. As shown in FIGS. 1A-1B, the perianal support apparatus 100, also referred to herein as a perianal support device 100, includes generally a central support element 102, a first compression element 104 extending laterally in a first direction away from the central support element 102, and a second compression element 106 extending laterally in a second direction from the central support element 102, different than the first direction. The first compression element 104 includes a proximal portion 108 (proximal to the central support element 102), a distal portion 112, a distal end 120, an outer surface 134 (that, e.g., is configured to face the tissue of a patient when in use), an inner surface 130 (that, e.g., is configured to face away from the patient when in use), and a gripping portion 116 at the distal end 120 of the first compression element 104 (as best seen in the perspective view of FIG. 1B). The second compression element 106 includes a proximal portion 110 (proximal to the central support element 102), a distal portion 114, an outer surface 128 (that, e.g., is configured to face the tissue of a patient when in use), an inner surface 132 (that, e.g., is configured to face away from the patient when in use), and a gripping portion 118 at the distal end 122 of the second compression element 106 (as best seen in the perspective view of FIG. 1A).

Figure 4:
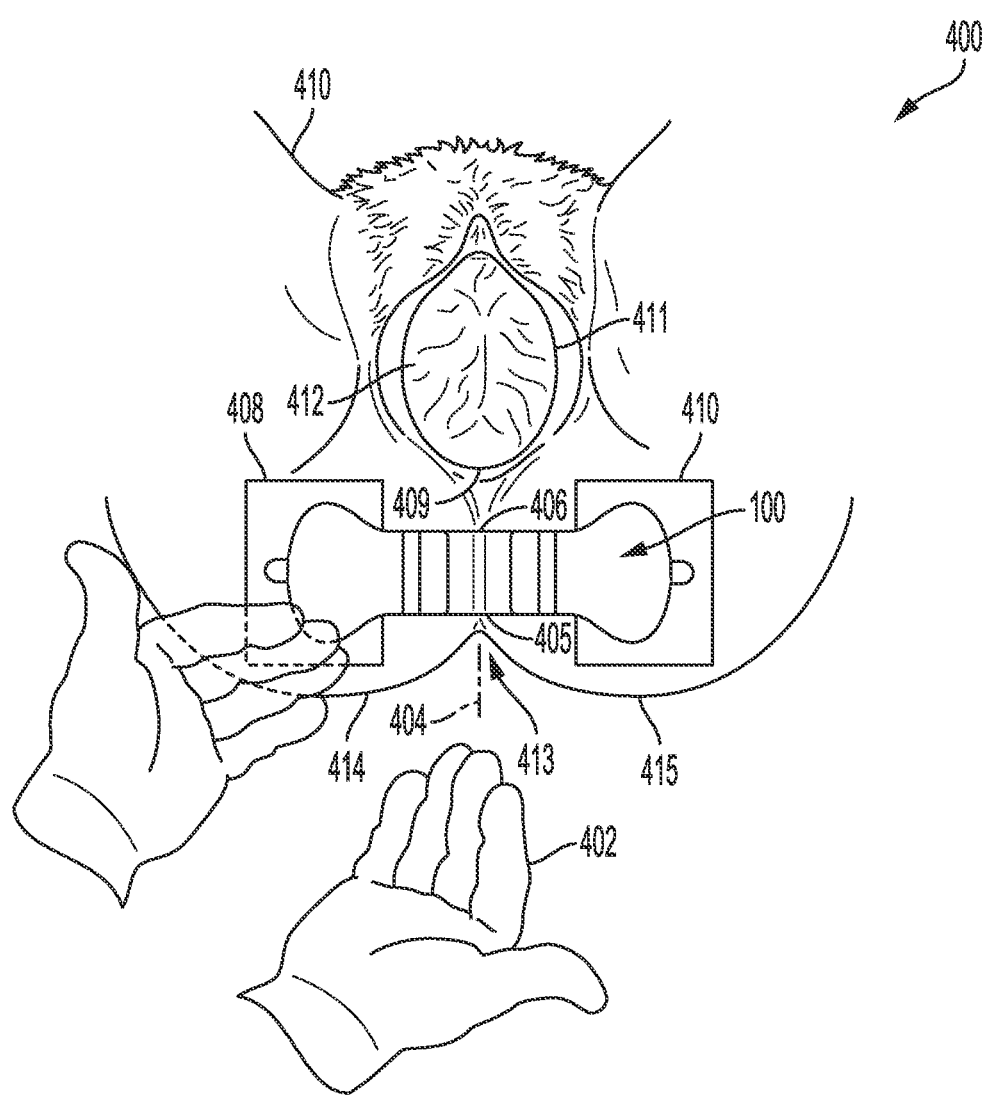
FIG. 4 is a partial perspective view of a perianal support apparatus applied to a patient during child delivery according to aspects of the present disclosure.

The central support element 102 may have a continuous compression surface apex that is sized to span across an anal orifice of a patient, and extend sufficiently beyond the anal orifice to engage with at least a portion of the external perianal tissue on opposing medial sides of the anal orifice when applied to the patient. The upper surface of the central support element 102, facing the patient when applied (as opposed to the concave portion 126 on the other side of the perianal support device 100 facing away from the patient during use) and generally referred to herein as the contact surface 124, may be anatomically configured to not enter the anal canal but rather have a generally a convex, curved surface (when viewed from one of the ends, as seen in FIG. 1E, and to an extent in the perspective views of 1A and 1B) with a radius of curvature sized to substantially prevent the apex of the central support element 102 from entering the anal canal of the patient. The contact surface 124, and in particular the compression surface apex of the central support element 102, may be oriented to extend along a first direction in a sagittal plane of the patient when the perianal support device 100 is positioned within the gluteal cleft of the patient. As shown in FIG. 4 (and discussed further below), the contact surface 124 extends along a midline axis 404 extending longitudinally between a posterior edge 405 and an anterior edge 406 of the perianal support device 100.

The contact surface 124 at the apex of the central support element 102 may be, for example, a pad. The contact surface 124 may be dimensioned to extend from end to end of the central support element 102 (e.g., along the compression surface apex) as well as a small distance along the outer surfaces 134 and 128 at proximal portions 108 and 110 of compression elements 104 and 106, respectively. The length along the compression surface apex may be on the order of 4 to 10 cm, for example approximately 5 cm. The contact surface 124 may be disposed and arranged as an interfacing structure disposed between the central support element 102 and the patient's perianal tissue (shown in FIG. 3) when positioned in contact with the patient.

In some embodiments, the contact surface 124 comprises an anatomically conformable structure. For example, the contact surface 124 may comprise a compliant pad. In some instances, the pad may be formed of a compliant material such as, by way of non-limiting example, polyurethane, silicon, rubber, foam, or cotton. Such materials may enable the pad to conform to the patient's anatomy as the perianal support device 100 is positioned in contact with the patient. In some embodiments, the pad is formed of a material that retains its shape (e.g., a complementary shape to the patient's tissue surface) upon removal of the pad from the patient's tissue. For example, in some embodiments, the pad is formed of a clay or clay-like polymer that has a high degree of conformability when pushed against the patient, but retained that "conformed" shape upon removal of the pad from the patient. In some embodiments, the pad is a sterile gauze pad, such as a nonwoven spun polyethylene gauze pad. In other embodiments, the pad includes an internal cushioning structure, such as polyurethane, silicon, rubber, foam, cotton, etc., with a non-abrasive skin contact surface. In other examples, the compliant pad may be formed by a layering of different materials, for example a foam adhered to the central support element 102 across the majority of the apex, in place between the base of the central support element 102 and an upper pad, such as a sterile gauze pad, which comes in contact with tissues of the patient. Further layers may be included as well to achieve a desired level of density/conformability in the padding at the apex of the central support element 102. In other examples, a density of the foam layer may be selected (e.g., more dense or less dense) to provide a desired level of conformability.

In other instances, the pad of the contact surface 124 comprises a hollow, inflatable structure that may be selectively inflated with various amounts of fluids (e.g., by way of non-limiting example, air, liquid, gels). In some embodiments, the pad may be adjusted by the user to exhibit different degrees of conformability. For example, the pad may be inflated through a tube that may be attached to the pad from a fluid source. In some embodiments, the tube is a detachable tube that may be removed or disengaged from the pad and/or the fluid source. In some embodiments, the fluid source comprises a pump-like structure which may be electronically or manually operated to increase or decrease the amount of fluid within the pad. In some embodiments, the fluid source includes a control feature that allows the user to control the fluid ingress and/or egress from the pad. In some instances, increasing the amount of fluid within the pad will increase the turgidity and lessen the degree of conformability of the pad. If the user fills the pad with fluid, the pad may hold its shape and stop conforming to the patient's tissue contours. If, however, the pad is incompletely filled with fluid, the pad may retain a high degree of conformability and assume a complementary shape to the contours of the patient's tissue as the perianal support device 100 is positioned in contact with the patient.

In some instances, the pad of the contact surface 124 may be opaque, while in other instances, the pad may be clear or translucent, thereby allowing the user to visually observe changes in tissue distension through the pad (i.e., by observing changes in the area of tissue contact against the pad over time). The pad may be adhered to the central support element 102 across the majority of the apex. In one embodiment, the pad may be die cut from stock materials. In another embodiment, pad may be an absorbent material adapted to absorb bodily fluids. It will be appreciated that the pad may make placement and application of perianal support device 100 more comfortable for the patient. In addition, the surface of the pad may be configured to frictionally engage the patient's perianal tissue to inhibit movement between the contact surface 124 and the patient. In still a further aspect, the pad may include a treating compound that can be disposed within the pad, applied on the surface, or a combination of both. Some examples of treating compounds may include, but without limitation to other compounds, antibacterial compounds, antibiotic compounds, sclerants, antimicrobial compounds, anti-inflammatory compounds, anti-fungal agents, anti-itching agents, humicants, moisture absorbing agents, gas absorbing agents, buffering agents for pH control, drying agents and the like and coagulants.

Figure 1C:
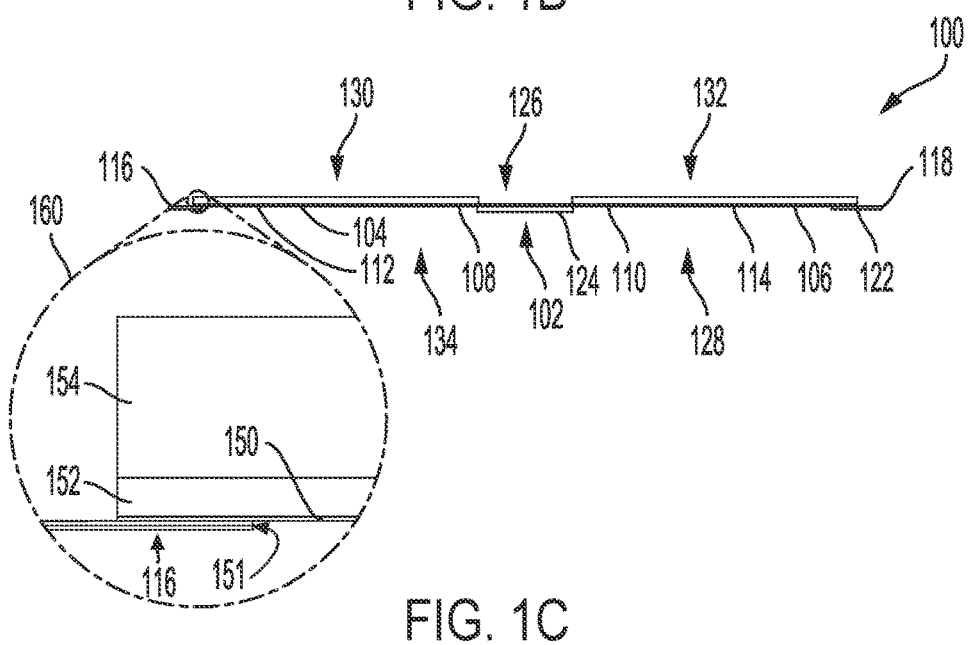
FIG. 1C is a flattened end view of a perianal support apparatus according to aspects of the present disclosure.

Referring now to FIG. 1C, illustrated is a flattened end view of the perianal support apparatus 100 according to aspects of the present disclosure. In other words, FIG. 1C illustrates the perianal support device 100 shown in FIGS. 1A-1B, with the first compression element 104 and the second compression element 106 flat relative to the central support element 102. This is for illustration purposes only. In particular, FIG. 1C illustrates a cross-sectional view of the device 100, as shown by close-up 160. Close-up 160 is taken from the distal end 120 of first compression element 104. As shown in close-up 160, the perianal support device 100 may be formed from three layers of material, first layer 150, second layer 152, and third layer 154. A cross section of a portion of gripping portion 116 is illustrated in the close-up 160 as well.

In general, the perianal support device 100 may be formed of biocompatible material suitable for contact with human tissue. Moreover, in one embodiment, the system is provided sterile in a package for single use application on a patient, although reusable devices according to the present teachings are also disclosed in the present description. For example, the first layer 150 may be formed of one portion of a hook and loop fastening system (the other portion being part of an anchor pad assembly, see FIG. 2, and also the other portion being part of the gripping portion, as shown in FIG. 1C as well and discussed below). The first layer 150 may be the loop side of the hook and loop fastening system in order to promote comfort as the first layer 150 constitutes the outer surface 134 and 128 of each of the first and second compression elements 104, 106 respectively when applied to a patient. Alternatively, the first layer 150 may be a releasable adhesive coating that can releasably adhere to the patient's skin (e.g., can be peeled from the patient's skin without tissue damage) or to an anchor pad (see FIG. 2). An example adhesive may be a Rayon woven tape on a liner. Another example may be a polyacrylate adhesive. Other examples of suitable adhesives include, without limitation, acrylic adhesives, silicone based adhesives, urethane adhesives, synthetic or natural rubber adhesives, among others. In some implementations, the adhesive may be configured to easily release from the patient's skin with minimal damage or soreness after a medical procedure is complete. In some implementations, prior to use, the adhesive faces a non-stick removable backing that can be peeled away to reveal the adhesive.

In the illustrated example, the gripping portion 116 is formed of a hook-type portion 151 of a hook and loop system or other type of adhering mechanism (e.g., the hook-type corresponding to the loop side of the hook and loop fastening system of the first layer 150, such that the gripping portion 116 may releasably connect with the surface of the compression elements 104, 106. For example, the gripping portion 116 illustrated in close-up 160 is formed by taking two same-sized pieces of hook material and adhering their backs to each other, so that both sides of the gripping portion have hook material facing outwards. The gripping portion 118 may be similarly formed.

The second layer 152 may be formed of a relatively rigid material, such as a thin sheet of polycarbonate. For example, the sheet of polycarbonate may have a thickness on the order of between 20 thousandths and 50 thousandths of an inch, or 25 thousandths and 35 thousandths of an inch, such as 30 thousandths of an inch in an example. In some embodiments, the second layer 152 may be uniform from distal end 120, across central support element 102, to distal end 122. In some other embodiments, the second layer 152 may vary in thickness along the length from distal end 120 to distal end 122 (e.g., approximately 25 cm to 30 cm). For example, the second layer 152 may be thinner towards the distal ends 120 and 122, and thicker towards proximal portions 108, 110 and central support element 102 (e.g., with a gradient change in thickness along the length of the perianal support device 100, or in step-wise thickness changes). As an example, a thickness of the second layer 152 may be on the order of 10 to 20 thousandths of an inch at the distal ends 120, 122 and increase to 30 to 50 thousandths of an inch thick at the central support element 102. This is by way of example only.

The third layer 154 may be a foam, such as an ethylene-vinyl acetate (EVA) foam. The third layer 154 may be several times thicker than that of the second layer 152, which in turn may be several times thicker than that of the first layer 150. In other examples, the third layer 154 may be formed of another material such as polyurethane, silicon, rubber, or cotton (to name a few examples). In some examples, the third layer 154 may be optional.

In some examples, the perianal support device 100 may be formed by adhering or laminating one or both of the first layer 150 and the third layer 154 respectively to the second layer 152. For example, both layers may be adhered using an adhesive or other bonding method to the second layer 152. The first layer 150 and third layer 154 may be adhered to the second layer 152 while the second layer 152 is flat, such as illustrated in FIG. 1C. Thereafter, the second layer 152 may be heat formed to heat up the second layer 152 to bend the perianal support apparatus 100 into the v-shape (see, e.g., end view of FIG. 1E). The apex at the central support element 102, after heat treating and bending to the v-shape, does not revert back to its pre-bending shape.

Thus, the central support element 102 substantially retains the v-shape obtained during heat treatment, while the first compression element 104 and the second compression element 106 remain generally without bend as they extend away from the central support element 102. However, since the first and second compression elements 104, 106 are formed from a relatively thin rigid material (second layer 152), they have an ability to flex starting near the proximal portions 108, 110 of respective compression elements 104, 106. While described herein as being formed of polycarbonate material, second layer 152 may alternatively be formed of another material that is able to bend to form a durable v-shape as illustrated in FIG. 1E at the central support element 102 while retaining an ability to flex starting at the proximal portions 108, 110. Some example alternative materials for second layer 152 include polymers, metals, ceramics or combinations thereof. The materials can be or include alone or in combination: hard solids, soft solids, tacky solids, viscous fluid, porous material, woven fabric, braided constructions, or non-woven mesh. Examples of polymers include polyethylene, polyester, Nylon, Teflon, polypropylene, polycarbonate, acrylic, PVC, styrene, PEEK, etc. Examples of ceramics include alumina, zirconia, carbon, carbon fibers, graphites, etc. Examples of suitable metals include titanium, stainless steel, cobalt-chrome, etc.

Figure 1D:
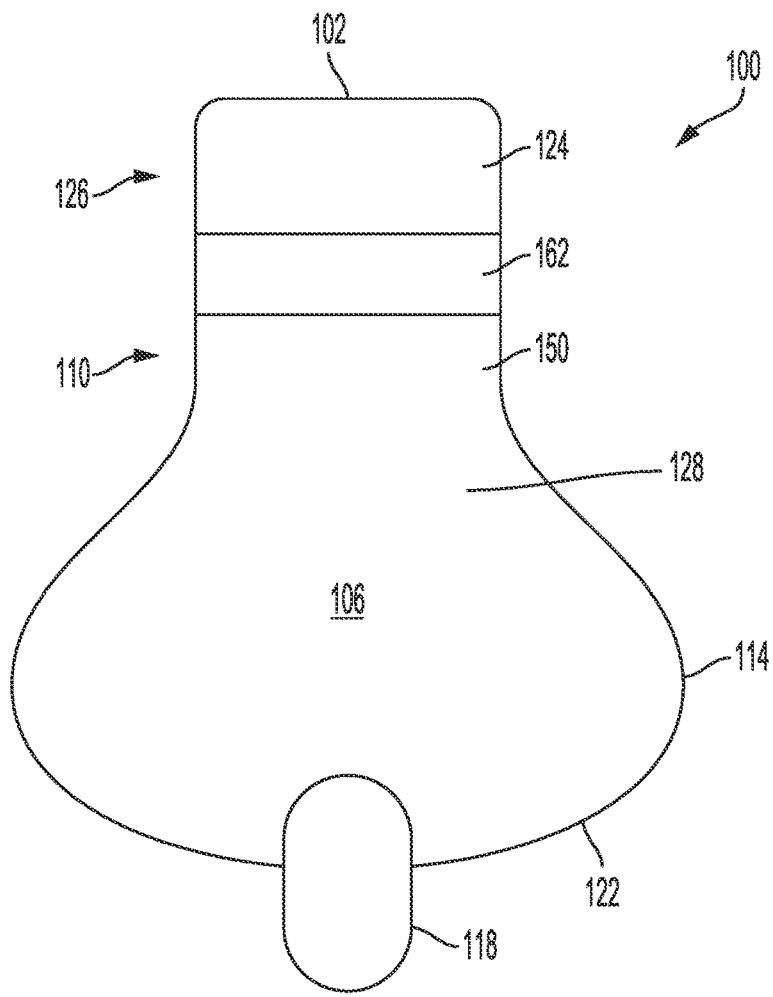
FIG. 1D is a side view of a perianal support apparatus according to aspects of the present disclosure.
Figure 1E:
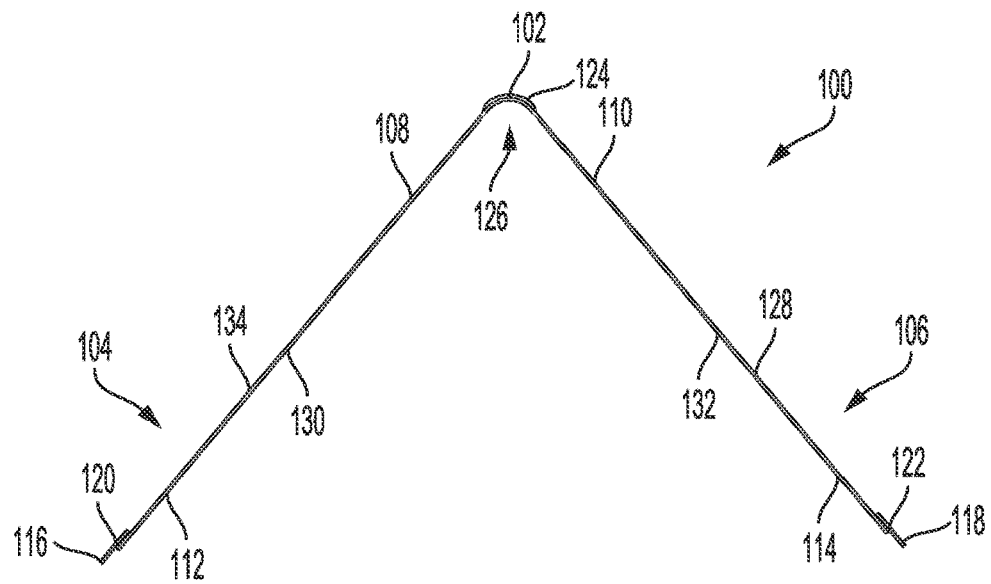
FIG. 1E is an end view of a perianal support apparatus according to aspects of the present disclosure.

Referring now to FIG. 1D, a side view of perianal support apparatus 100 is illustrated according to aspects of the present disclosure. The side view is of second compression element 106; while not illustrated, first compression element 104 would be described in similar manner as below with respect to FIG. 1D, because compression elements 104, 106 are formed in the same shape and may be mirror images of each other.

The outer surface 128 may be first layer 150 and may be formed of a loop side of a hook and loop fastening system (since outer surface 128 is the surface facing/touching the patient when applied). Region 162 illustrates, generally, the flex region starting near proximal portion 110 between the remainder of the compression element 106 and the central support element 102. The flex region 162 may have the same first layer 150 extending therealong, or alternatively may have a different material, such as a foam or gauze material. In some examples, the flex region 162 may have the loop material of first layer 150 extending entirely below it (e.g., such that the first layer 150 extends continuously from distal end 122 to distal end 120), with an additional layer of gauze or other absorbent material just at flex region 162. For example, the additional layer may be of a thinner layer of gauze than that used for contact surface 124.

The dimensions of compression element 106 may vary along the length of the compression element 106 as it extends from proximal portion 110 to distal portion 114. As illustrated, the width of the proximal portion 110 is less than the width of the distal portion 114, such that the side view of the perianal support device 102 assumes a wing-like, or barbell-like, shape. While shown as curved edges extending from the proximal portion 110 to the distal portion 114, alternatively the edges may assume a more linear shape, such that the distal portion 114 assumes a more box-like shape. Either way, having the proximal portion 110 being smaller in width than the distal portion 114 provides benefits, such as maintaining a proper size for the compression element 102 when applied to the tissues of the pelvic floor of a patient extending from posterior to anterior of the anal orifice of the patient without interfering with the vaginal opening during childbirth. Further, the larger size of the distal portion 114 provides a larger area with which to anchor the perianal support device 102 to portions of the patient, such as generally the crowns of the buttocks of the patient (other regions closer in the gluteal cleft, or approximately past the crown of the buttocks, though still near, are contemplated as well).

Also illustrated at the distal end 122 of compression element 106 is a gripping portion 118 (which may also be referred to as a tab, thumb tab, or grasping point). The gripping portion 118 may be formed separately from the rest of the perianal support device 102. For example, the gripping portion 118 may be formed by cutting two same-sized pieces from a hook portion of a hook and loop fastening system (so that it may interface with the other side of the same hook and loop fastening system of first layer 150), and adhering the two pieces (non-hook side) together. Alternatively, the two pieces may be joined via other mechanisms, such as stitching, tape, heat sealing, etc. The gripping portion 118 may therefore be releasably engageable with the outer surface 128 of the compression element 106.

For example, when engaged, the gripping portion 118 may be placed (as illustrated throughout FIGS. 1A-1G, but particularly in FIG. 1D) so that a first region is connected to the outer surface 128 at distal end 122, and a second region protrudes beyond the distal end 122 for grasping by a user. In use, for example, a user (such as a physician) may grab the gripping portion 118 and manually position the compression element 106 on the buttocks of the patient, with the compression element 106 bending starting generally at the flex region 162 to follow the contour of the patient's buttock to a crown of the buttock, where the distal portion 114 may be releasably adhered to the general area of the crown of the buttock, either directly to the buttock or to an anchor pad (see, e.g., FIG. 2). Further, after placement the user may again grasp the region of gripping portion 118 extending beyond the distal end 122, gently lift the distal portion 114 of compression element 106, and reposition the distal portion 122 to the desired location generally in the area of the crown of the buttocks. In this manner, the user may adjust the compressive force applied through the compression member 106. As noted above, this discussion related to FIG. 1D is equally applicable to the aspects related to compression element 104, though not expressly illustrated in FIG. 1D.

Further, because the gripping portion 118 is formed in one aspect of a material that releasably engages with the outer surface 128 of the compression element 106 (i.e., the first layer 150, see FIG. 1C), a user is also able to remove the gripping portion 118 from the outer surface 128 and reposition the gripping portion 118 relative to the compression element 106. Examples of repositioning may include placing less of the first region over the outer surface 128, leaving more second region beyond the distal end 122 for grasping. Another example may include placing the first region of the gripping portion 118 at a different location along the length of the distal end 122 of the compression element 106 in order to obtain a potentially more advantageous point of manipulation of the compression element 106 relative to the patient. While in some examples the hook part of a hook and loop fastening system covers the full surface of the gripping portion 118, in some other examples only a part of the gripping portion 118 may have the hook material covering it, with the remainder being formed of a similar or same substrate as the hook portion, but without the hook feature. For example, approximately half of the gripping portion 118 may include the hook feature with the other half without the hook feature. In this manner, the gripping portion 118 is still connectable to the outer surface 128, while leaving a section that is easier to grasp (e.g., a section of the gripping portion 118 that will more smoothly interface with a hook surface of an anchor pad). Either way, the gripping portion 118 may be easily grasped, pulled, and quickly detach and either reposition or remove the perianal support device 102 from the patient.

Finally, although described as being separate from the perianal support device 102, in some embodiments the gripping portion 118 may be integrally formed with the at least some aspects of the rest of the perianal support device 102. For example, the gripping portion 118 may include the layers illustrated in the close-up 160 (FIG. 1C)— first layer 150, second layer 152, and third layer 154. Thus, the gripping portion 118 may be formed with the rest of the perianal support device 100 when shaped/cut from a sheet of material (e.g., after the first and third layers have been adhered to the second layer). Alternatively, the gripping portion 118 may include just first layer 150, or first layer 150 and third layer 154. In such scenarios, the gripping portion 118 may be formed after the second layer 152 is shaped/cut from a sheet of material. In some examples where the gripping portion 118 is integrally formed with the rest of the perianal support device, the first layer 150 may extend a length beyond the distal end 122 of compression element 106, but stop before reaching the distal end of the gripping portion 118. This may leave a section of the gripping portion 118 that, again, will more smoothly interface with a hook surface of an anchor pad. In yet other examples, the first layer 150 may extend beyond the distal end 122 of compression element 106 to the distal end of the gripping portion 118, such that the gripping portion 118 is formed of the first material 150 only.

Figure 1F:
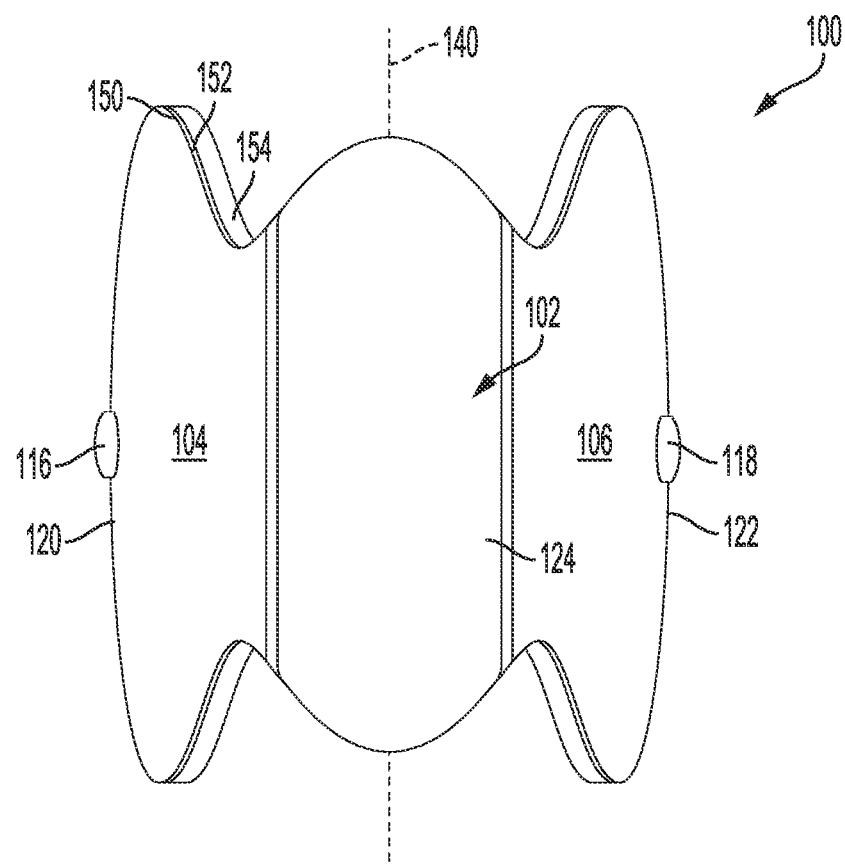
FIG. 1F is a top view of a perianal support apparatus according to aspects of the present disclosure.
Figure 1G:
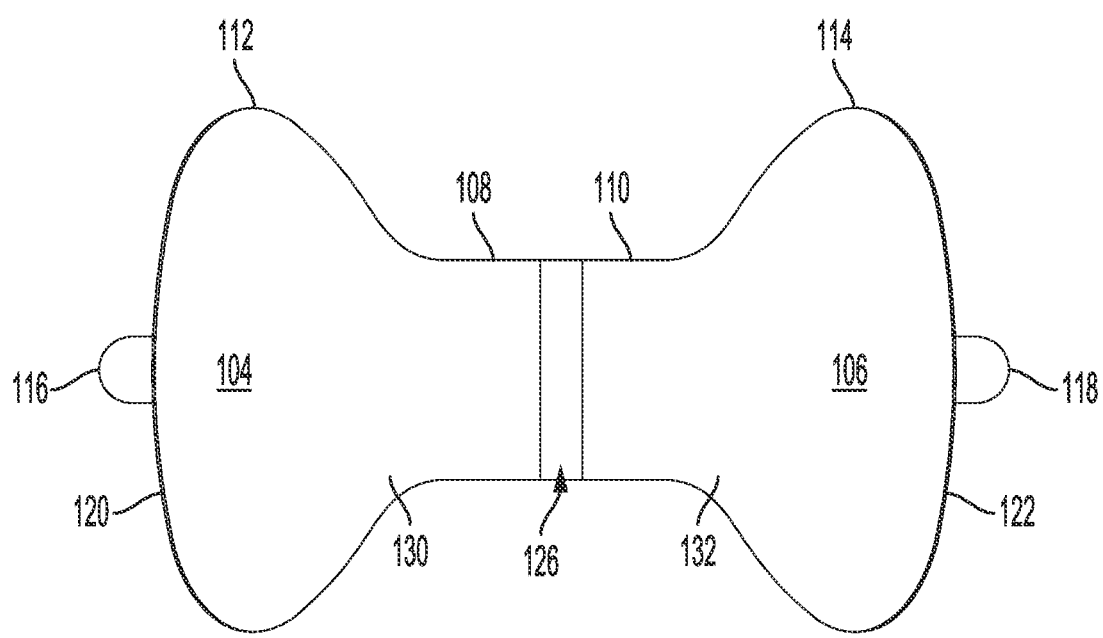
FIG. 1G is a bottom view of a perianal support apparatus according to aspects of the present disclosure.

Turning now to FIGS. 1F and 1G, illustrated are top and bottom views, respectively, of the perianal support device 100 according to aspects of the present disclosure. As illustrated in FIG. 1F, the contact surface 124 extends from the central support element 102 to proximal portions 108, 110 of compression elements 104, 106 respectively. A continuous compression surface apex of the central support element 102 may extend along a midline axis 140, the axis along which may be oriented to extend along a first direction in a sagittal plane of the patient when the perianal support device 100 is positioned within the gluteal cleft of the patient.

Figure 2:
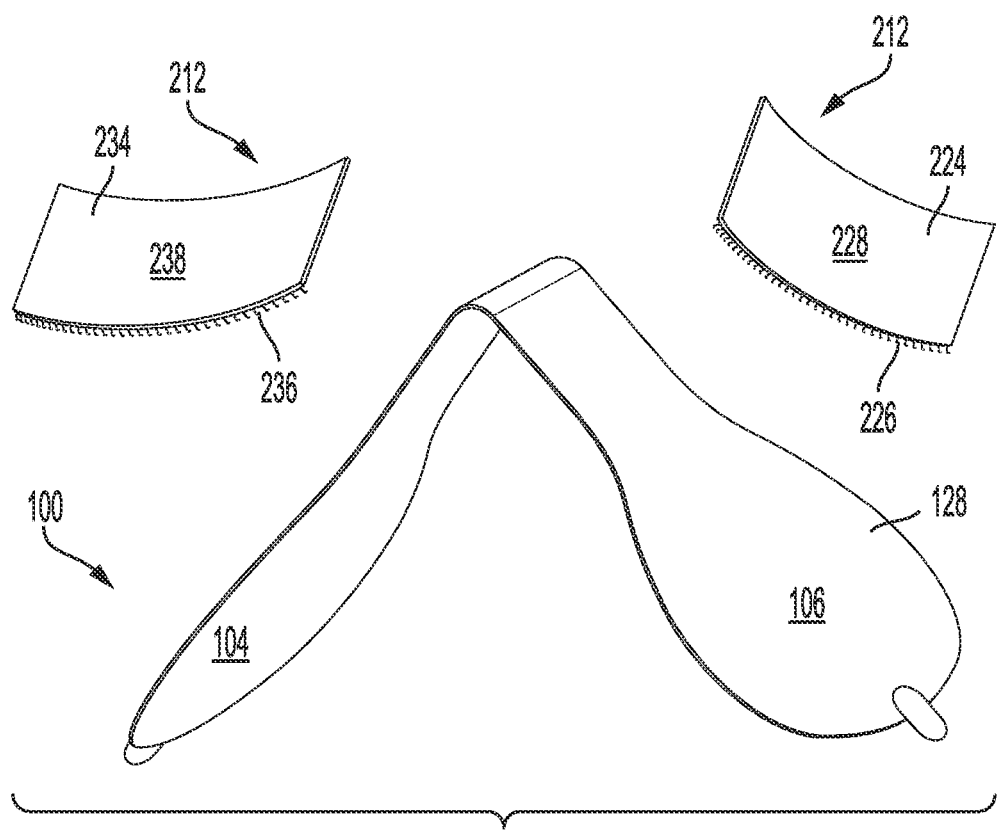
FIG. 2 is a perspective view of a perianal support apparatus including exemplary securing members according to aspects of the present disclosure.

FIG. 2 is a perspective view of the perianal support apparatus 100 including exemplary securing members according to aspects of the present disclosure. In particular, FIG. 2 illustrates the perianal support device 100 interfacing with two anchor pads 228 and 238. In this example, the first compression element 104 includes a first half of a releasable fastening system on outer surface 134, such as a hook and loop system or a releasable adhesive system. In the illustrated embodiment, the anchor pad 238 has a generally rectangular shape that is shorter in length and wider than the first compression element 104. The shape of the anchor pad 238 is shown for illustration purposes and may take any form that is suitable for fixing to a patient (such as the crown of the buttocks of the patient), as well as joining to the first compression element 104. For example, the shape of the anchor pad 238 may be a circular or oval shape. In like manner, the second compression element 106 includes the same type of first half of the releasable fastening system on outer surface 128, such as a hook and loop system or a releasable adhesive system. In the illustrated embodiment, the anchor pad 228 also has a generally rectangular shape that is shorter in length and wider than the second compression element 106. The shape of the anchor pad 228 is shown for illustration purposes and may take any form that is suitable for fixing to a patient (such as the crown of the buttocks of the patient), as well as joining to the second compression element 106, such as circular or oval as well.

Looking first at the anchor pad 238, it includes a first surface 234 having an adhesive surface adapted for joining to the patient's skin. The opposing surface 236 includes the second half of the releasable fastening system (e.g., the hook portion of the hook and loop system) to releasably engage with the outer surface 134 of the first compression element 104 of the perianal support device 102. In a similar manner, the anchor pad 228 includes a first surface 224 having an adhesive surface adapted for joining to the patient's skin. Examples of adhesives, as noted above, may include polyacrylate adhesives, acrylic adhesives, silicone based adhesives, urethane adhesives, synthetic or natural rubber adhesives, among others. In some implementations, the adhesive may be configured to easily release from the patient's skin with minimal damage or soreness after a medical procedure is complete. In some implementations, prior to use, the adhesive faces a non-stick removable backing that can be peeled away to reveal the adhesive. For example, the adhesive of the surfaces 224, 234 may be selected to have material properties permitting it to be peeled from the patient's skin after the procedure is complete by pulling a corner or edge from the skin at an angle from the skin within a range from about 10 to 170 degrees while maintaining skin integrity, or without damaging the skin. In some implementations, the adhesive is a body worn medical adhesive from any of a variety of adhesive providers. The opposing surface 226 includes the second half of the releasable fastening system (e.g., the hook portion of the hook and loop system) to releasably engage with the outer surface 128 of the second compression element 106.

In some embodiments, instead of using the hook and loop fastener arrangement discussed above, at least a portion of a surfaces 183, 187 of the securing members 106, 107 has an adhesive coating adapted for joining to a fixed object. At least a portion of the outer surfaces 134, 128 may include an adhesive coating that can fix the compression elements 104, 106 to another object. For example, the adhesive coating may be adapted for releasably adhering to a patient's skin, such as generally the crowns of the buttocks. In another embodiment, the adhesive may be adapted for joining to another object, such as anchor pads 238, 228 of FIG. 2 (which, in turn, may be adhered to surfaces of the patient's skin such as generally the crowns of the buttocks). In this manner, the securing member can fix the position of the perianal support device 100 to the patient.

Aspects of the present disclosure, described with respect to FIGS. 1A-2 above and further with respect to FIGS. 3-5 below, further contemplate a kit that includes one or more of the components described above provided in a package. In one embodiment, the kit includes at least a sterilized perianal support device 100 and anchor pads 228, 238 as described above. In the unassembled kit, a health care provider can remove the perianal support device 100 and anchor pads 228, 238 from the packaging and assemble system. In still a further embodiment, the kit includes a treating compound to apply to the patient. In one such embodiment, the treating compound is provided in a separate package. In an alternative embodiment, the treating compound is applied to or incorporated into the perianal support device 100, e.g., on the contact surface 124.

Figure 3:
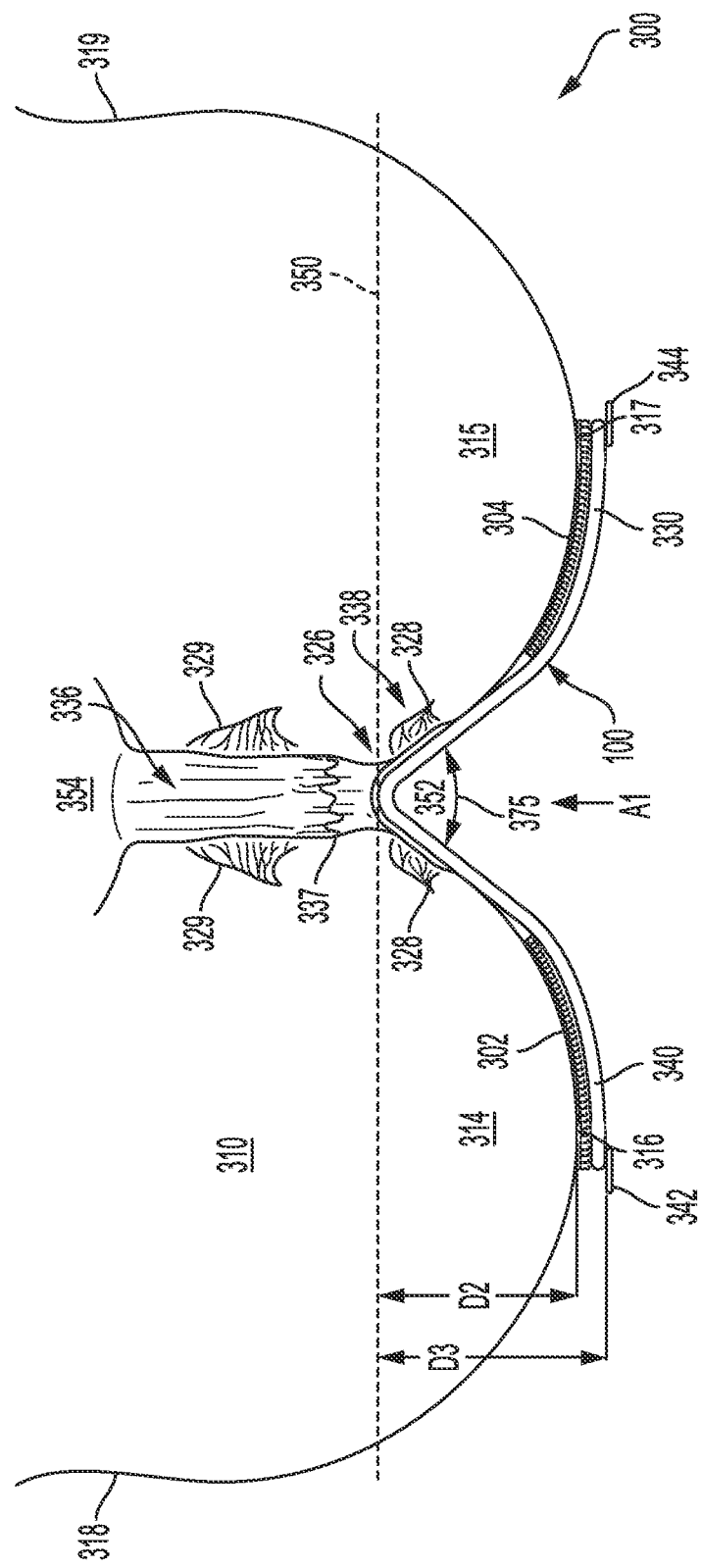
FIG. 3 is a partial cross sectional end view showing stylized patient anatomy and the applied perianal support apparatus according to aspects of the present disclosure.

Referring now to FIGS. 3-4, a support system according to embodiments of the present disclosure is illustrated in association with the perianal tissue of a patient 310 (FIG. 3). FIGS. 3 and 4 show the perianal support device 100 in association with the perianal tissue of a patient 310.

In FIG. 3, the patient 310 is shown in partial cross section to illustrate a portion of the rectum 354, anal canal 336, anal orifice 326, internal venous plexus 329, pectinate line 337 (also known as the dentate line), and external venous plexus 328. The patient's buttocks 314 and 315 are shown with the crowns of the buttocks 316 and 317, respectively, laterally adjacent the perianal region 338. The gluteal cleft 413 (FIG. 4) is between the buttocks 314 and 315. The buttocks 314 and 315 extend laterally beyond crowns 316 and 317 toward lateral flanks 318 and 319, respectively. The crowns 316 and 317 of each buttock 314 and 315 in essence define the midline of each leg and the lateral flanks 318 and 319 are the area lateral of the leg/buttocks midline. The lateral flanks 318 and 319 may include, for example but without limitation, all or a portion of the lateral buttocks, hips, or upper thigh of the patient.

FIG. 4 illustrates the patient 410 (patient 310 in FIG. 3) during a child birthing process. Contractions during labor move a child 412 into the birth canal and ultimately, for a vaginal delivery, through the vaginal opening 411, as shown in FIG. 4. In an alternative birthing process, labor is commenced to move the child 412, but for a variety of reasons, the delivery does not occur vaginally but instead caesarian delivery is performed through a surgical opening in the mother's abdomen. During the birthing process, tremendous pressure is exerted (e.g., generated by voluntary and involuntary muscle contractions) in an effort to move the child 412 toward delivery through the vaginal opening 411. At least some of this pressure is exerted against the tissues adjacent the anal orifice 326 in the perianal region 338. The result of these forces is that blood vessels near the anus, such as those in the external venous plexus 328, may bulge or rupture causing hemorrhoids or increasing their severity. Still further, other tissues in the perianal region 338 adjacent the anus may distend outwardly opposite arrow A1 in FIG. 3 causing lacerations such as tearing around the vaginal opening or fissures from the anus. In addition to the blood loss, pain, and discomfort, these lacerations can be a location for infections in the mother.

Aspects of the present disclosure provide devices to support the perianal tissues during the birthing process without interfering with the birthing canal or vaginal opening 411 and/or allowing easy removal to access the perianal region 338. Still further, methods are provided to support the perianal tissue to inhibit damage to the tissue near the anal orifice 326, both internally and externally, to inhibit, for example but without limitation to other actions, the formation or advancement of external hemorrhoids and/or to inhibit the formation or advancement of lacerations of the perianal tissues. By applying counter pressure with the perianal support device 100 in the opposite direction to the perianal region 338 and the anal orifice 326 (FIG. 3), a user (e.g., a healthcare practitioner or the patient 310) can provide the patient 310 with a tactile, discrete source of resistance against which to push and support pelvic floor tissues to direct forces applied to the baby toward the vaginal opening 411 (FIG. 4).

Referring again to FIG. 3, in use, a health care provider positions the patient 310 to expose the perianal region. In the child birthing process, the patient 310 may be positioned in stirrups attached to a delivery table. Anchor pads 302 and 304 are adhered to the patient's skin on the general region of the patient's buttocks 316 and 317, respectively (see also anchor pads 408 and 410 of FIG. 4, corresponding to anchor pads 302 and 304 of FIG. 3, respectively). The perianal support device 100 is then moved adjacent the gluteal cleft 413 (FIG. 4) between buttocks 414, 415. The midline 404 of the perianal support device 100 is generally aligned with the patient midline within the sagittal plane.

The perianal support device 100 is advanced in the direction of arrow A1 (FIG. 3) toward the anal orifice 326 (generally within the sagittal plane) to bring the contact surface of perianal support device 100 into contact with the perianal tissues. Continued advancement of the support device toward the anal canal applies pressure through the contact surface 124 of the central support element 102 (FIGS. 1A-1G) to the perianal tissues (also potentially referred to as perivaginal tissue or, more generally, tissues of or associated with the pelvic floor; this may refer to those muscles, skin, soft tissue, and nerves at, surrounding, adjacent, or near the vaginal opening or anus of a patient). In one aspect, the healthcare provider places at least one finger within the access cavity 352 (FIG. 3) to advance the perianal support device 100 against the anal orifice. In another aspect, an instrument having complimentary engagement surface to at least a portion of the access cavity 352 is used to apply pressure to the perianal support device 100. With continued pressure applied to the access cavity 352, the distal end of the compression element 340 (e.g., 104 of FIG. 1A) is extended laterally of the anal orifice 326 out of the gluteal cleft 413 (FIG. 4) and releasably attached to anchor pad 302 placed generally over the crown of the buttocks 316 (e.g., using tab 342). In a similar manner, with compressive force still applied by the healthcare provider to support perianal support device 100, the distal end of the compression element 330 (e.g., 106 of FIG. 1A) is extended laterally of the anal orifice 326 out of the gluteal cleft 413 (FIG. 4) and is secured to anchor pad 304 placed generally over the crown of the buttocks 317 (e.g., using tab 344).

The extent of tissue deformation surrounding the anal orifice 326 is a function of the patient anatomy and of the amount of compressive force applied during application of the perianal support device 100. In one aspect, the health care provider makes initial contact with anal orifice 326 and then applies pressure in the sagittal plane (generally toward the patient's head) to advance the device 1 cm to 3 cm. This advancement of the device approximately 1 cm to 3 cm compresses the perianal tissue and thereby supports the tissue to inhibit distention as the patient pushes during the birthing process. It will be appreciated that with the illustrated embodiment, the healthcare provider may reposition the device and adjust the compressive force applied through the compression elements 330 and 340 to the central support element of the perianal support device 100 by releasing or adjusting the attachment between the anchor pads 302, 304 and the compression elements 340, 330 (respectively).

In an alternative approach, the contact surface 124 is positioned in engagement with the anal orifice 326 with little if any compressive force applied to deform the perianal tissue. The support device is then secured in position as described above. With this technique, the support device will resist movement of the device in a direction generally away from the patient's head and will thereby support the perianal tissue to maintain its position.

As shown in FIG. 3, the distance D2 between the anal orifice 326 and the buttocks crown 316 is almost equal to the distance D3 between the distal end of compression element 340 and the anal orifice 326, with just the depth of the anchor pads 304, 302 and of compression elements 330, 340 (e.g., including layers 150, 152, and 154) providing a difference between D3 and D2. The distance D3 represents the length or extent of the compression element 340 as measured in the sagittal plane. Thus, tension is transferred through compression element 340 to exert a compressive force on the contact surface 124 of the perianal support device 100. This illustrates the manner in which the compression elements 330, 340 are able to conform to the contours of the crowns of the buttocks 316 and 317.

Referring again to FIG. 4, with perianal support device 100 in position, a healthcare provider is allowed to position one or both hands 402 within the access cavity 352 extending into the gluteal cleft 413. In this manner, the hands 402 may be below the lowest portion of the vaginal opening 411 as the head of the baby 412 passes out of the vagina. Thus, the hand within the access cavity 352 is positionable less than 1 cm from the mother's vaginal opening 411 or perineum so the healthcare provider may support the head of the baby 412 as is it is being born. The position of first end 406 of the perianal support device 100 also allows access to the tissue immediately below the vaginal opening 411 in the event an obstetric maneuver, such as an episiotomy, manipulation of the fetus, etc., is necessary, while the second end 405 extends beyond the anal orifice of the patient. Further, as discussed above, in one aspect the perianal support device 100 is quickly repositioned or removed by releasing at least one of the compression elements 330, 340 (FIG. 3) from the anchor pads 304, 302 (e.g., by grabbing at least one corresponding gripping portion, such as 116, 118 of FIGS. 1A-1G), an obstetric maneuver is performed, the perianal support device 100 is repositioned in a supporting position adjacent the anus and the compression elements 330, 340 are repositioned on the anchor pads 304, 302.

Of particular note, as best seen in FIG. 4, the anchor pads 408 and 410 (corresponding to anchor pads 238 and 228 of FIG. 2) are placed generally over the crowns of the buttocks 414, 415. The perianal support device 100's first compression element 104 and second compression element 106 (FIG. 2) are placed over the respective anchor pads 408 and 410 in FIG. 4. Because of the flexible nature of the perianal support device 100 beyond the proximal portions 108, 110, the first compression element 104 generally follows the contour of the patient's buttocks from the gluteal cleft 413 to the crown of the buttocks 414. In similar manner, the second compression element 106 generally follows the contour of the patient's buttocks from the gluteal cleft 413 to the crown of the buttocks 415. The gripping portions 116, 118 (FIG. 1A) provide additional area with which the healthcare provider may grasp the perianal support device 100 while placing the distal portions 112, 114 of the compression elements 104, 106 (FIG. 1A) over the anchor pads 408 and 410 (FIG. 4), respectively.

Because the perianal support device 100 does not require additional straps to attach it to the patient (or any other structure), but rather attaches the distal portions 112, 114 of the compression elements 104, 106 to suitably placed anchor pads, aspects of the present disclosure facilitate faster application to the patient. Moreover, because the distal ends 120, 122 of the compression elements 104, 106 respectively do not generally exceed the crown of the buttocks, the perianal support device 100 is not pulled away from contact with the perianal/pelvic floor during patient muscle contraction/movement.

Use of the described perianal support device may support the perianal tissue and/or anococcygeal region of a patient during labor, which may reduce the incidence of a number of complications and conditions, including, for example, pelvic floor incompetence or dysfunction (over-stretching of pelvic floor muscles, ligaments and tendons), organ prolapse results from the over stretching, incontinence secondary to pressure and stretching exerted on bladder and bladder neck, over-stretching due to use of forceps in delivery, perineum tears and lacerations due to over stretching, vacuum or forceps use, uncontrolled flexion/extension of the fetal head as it descends, and hemorrhoids. The pelvic floor, sometimes referred to as the pelvic diaphragm, is the inferior border of the pelvic cavity defined between the lower openings of the pelvic girdle. The pelvic floor has two hiatuses (gaps or openings): the anterior urogenital hiatus through which the urethra and vagina pass and the posterior rectal hiatus through which the anal canal passes. The pelvic floor facilitates birth by resisting the descent of the presenting part of the baby (i.e., typically the head of the baby), causing the baby to rotate forward to navigate through the pelvic girdle and exit through the vaginal opening in the anterior urogenital hiatus in the pelvic floor. In particular, the pelvic floor, the sacrum, and the coccyx provide resistance against the downward descent of the baby (along the longitudinal axis of the baby and toward the posterior rectal hiatus) caused by force of the mother's uterine contractions. This passive resistance causes the baby's head to rotate and descend in the direction of least resistance, which is usually in the direction of the midline of the maternal pelvis. Thus, pressure applied by the perianal support device 100 may apply pressure to and push against the skin of the anococcygeal and/or perianal tissues outside the pelvic floor to thereby support the internal pelvic floor tissues in their function of guiding the baby toward the vaginal opening. Support of the posterior pelvic floor by the devices disclosed herein facilitates the progression of the baby through the birth canal toward the vaginal opening by acting as a type of external scaffolding to lengthen the path of passive resistance that turns and guides the baby towards the vaginal opening.

Figure 5:
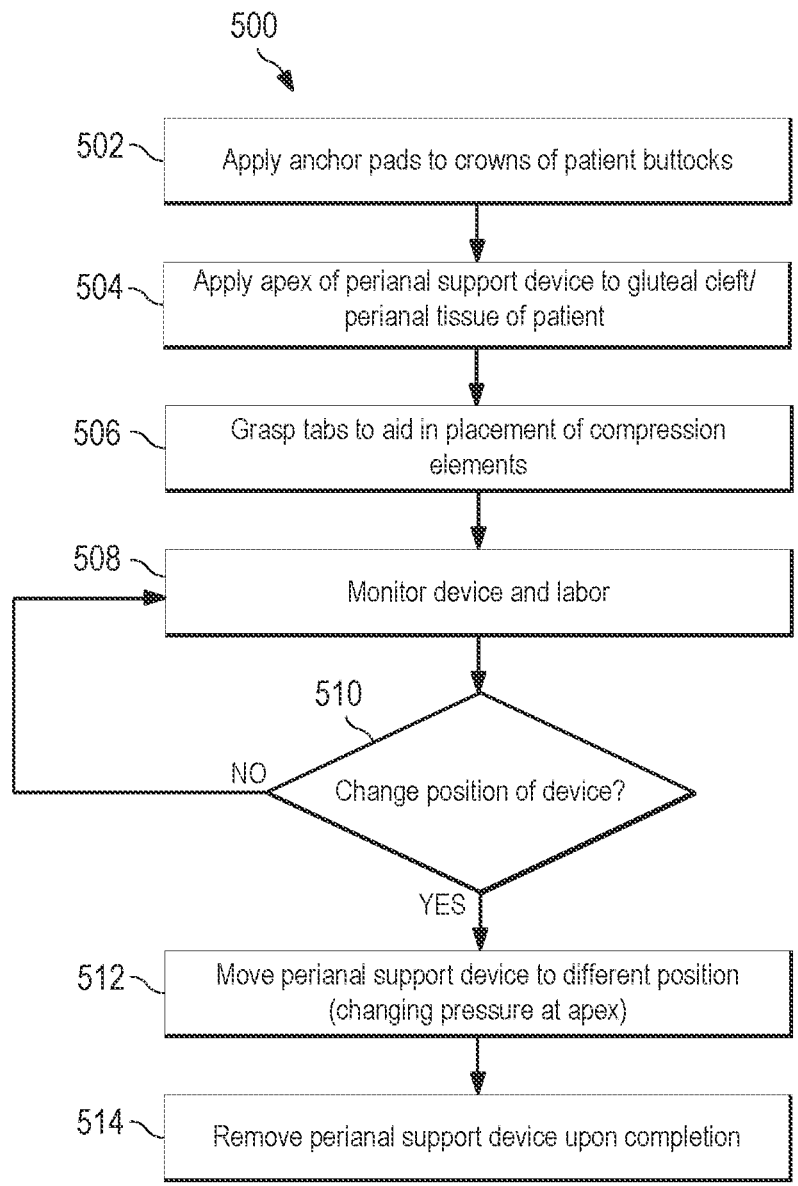
FIG. 5 is a flow chart illustrating a method of using a perianal support device according to aspects of the present disclosure.

Referring now to FIG. 5, there is a shown a flow chart illustrating a method 500 of utilizing a perianal support device 100 according to some aspects of the present disclosure to manage a mother's labor process to reduce the duration of second stage labor and increase the incidence of a vaginal delivery without increasing tissue damage to the mother. In general terms, the method includes applying the perianal support device 100 in engagement with the perianal tissue and monitoring the progression of labor during the second stage. The method 500 may be performed using one or more of the devices, systems, and kits described above, such as the perianal support device 100 and the anchor pads 238, 228 (FIG. 2). The method 500 may be performed by a person, such as a physician (e.g., doctor, nurse, surgical technician. It is understood that additional steps can be provided before, during, and after the steps of the method 500, and that some of the steps described can be replaced or eliminated for other embodiments of the method 500.

The method 500 may begin after determining whether the expecting mother has previously delivered a child by a vaginal delivery. If the answer to this inquiry is yes, the progress of labor is monitored to determine if labor is progressing as desired. The progression of labor may include the amount of movement of the child toward the vaginal opening over a given a period of time. Alternatively, the progression of labor may include shortening or thinning of the cervix, the amount of cervical dilation, assessment of fetal position and/or descent (e.g., via digital assessment inside the vagina, via manual palpation of the abdomen, via visual observation, or via imaging), and the amount of movement of the child toward the vaginal opening in comparison to the number of contractions or successful pushes the mother has experienced. The determination of the progression of labor may be made by a healthcare provider monitoring the patient or by an electronic monitoring system receiving one or more inputs indicative of labor progression such as the strength and/or number of contractions, effective pushes, and movement of the child within the mother and/or overall time of labor. As long as labor is progressing as desired, the progress of labor may be monitored before applying the perianal support device 100. In other examples, the perianal support device 100 may be applied while monitoring the progress of labor. Either way, application of the perianal support device 100 may proceed as described above and further below with respect to the method 500.

Further, if the answer to the inquiry was no (the mother has not had a successful vaginal delivery or has previously undergone a Cesarean section child delivery procedure), then the healthcare provider may determine to apply the perianal support device 100 as described above and further below with respect to the method 500.

At block 502, a user (e.g., medical staff) applies the anchor pads (e.g., anchor pads 302, 304 of FIG. 3) to the crowns of the patient's buttocks. To do this, the user may first peel off a liner/backing that covers the adhesive side of the anchor pads (e.g., the sides 234, 224 of anchor pads 238, 228 in FIG. 2), the backing being used to prevent premature adhesion of the adhesive on the backs of the anchor pads. While in some examples, the user applies the anchor pads to the crowns of the buttocks (i.e., one anchor pad to each crown) first, in other embodiments the user may place the perianal support device 100 in the approximate target location at the tissues of the pelvic floor/covering the anal orifice 326 and bend the compression elements 104, 106 to ascertain approximately the region of the buttocks on which to place the anchor pads. The perianal support device 100 may then be removed while the user places the anchor pads in the desired or determined locations. Where anchor pads are not used, e.g. there is adhesive on first layer 150 (FIG. 1C) instead of a loop portion of a hook and loop system, block 502 may be omitted in favor of adhering at least the distal portions 112, 114 (FIGS. 1A-1B) of compression elements 104, 106 directly to the buttocks in a desired location (see block 504).

At block 504, the user pushes the perianal support device 100 against the anus with a first hand. Specifically, the user pushes the apex of the central support element 102 against the anus, with the compression elements 104, 106 extending off to each side. The opposite hand may spread one of the patient's buttocks away from the device while the first hand pushes to get further compressive penetration in the gluteal cleft. The hands may then switch and the same action performed on the other buttock. Care is taken to ensure that the first end 406 (FIG. 4) is below the lowest portion 409 of the vaginal opening 411, as noted previously.

At block 506, the user grips the gripping portions 116, 118 of compression elements 104, 106 to guide the compression elements 104, 106 to place them on the buttocks. In some examples, the user will have previously placed the gripping portions 116, 118 on the desired locations at distal ends 120, 122 of compression elements 104, 106 (e.g., where the gripping portions 116, 118 are formed of a hook-type portion of a hook and loop system or other type of adhering mechanism). In other examples where the gripping portions 116, 118 are integrally formed with one or more layers of the perianal support device 100, the user will not have to first place the gripping portions 116, 118.

At block 508, the user maintains hold of the gripping portions 116, 118 that were grasped at block 506 and uses these as a primary mechanism by which to bend the compression elements 104, 106 over the contours of the patient's buttocks (extending out of the gluteal cleft while the central support device 102 is still being held against the anal tissue of the patient). This may be done one at a time, such that block 506 may occur for a first compression element, then block 508 for bending and placement of that compression element, and then blocks 506 and 508 may be repeated for the other compression element (after which method 500 may proceed to block 510). This may be done around the same time where another is available to assist with maintaining central support element 102 in place against the anal tissue of the patient. After conforming the compression element such that it bends, starting e.g. at flex region 162, outward to generally conform to the contour of the patient's buttock. The distal portion (e.g., 112 of compression element 104, FIG. 1A) may be adhered to the crown of the patient's buttock, either directly (where no anchor pad is used) or to some portion of the anchor pad (see block 502). This is repeated for the other compression element (106 when continuing the example).

At block 510, the user (or other assigned medical staff) monitors the position of the perianal support device 100 on the patient, how the perianal support device 100 responds to patient contractions (voluntary and/or involuntary muscle contractions), and/or patient feedback (if any, such as whether it is causing more pain, or aiding in tactile feedback, or nothing is felt, etc.) on comfort or utility of the current placement of the device. Further, the monitoring may also take into account the administration of sensory numbing medications administered to the patient. For example, since the application of numbing medications, including spinal epidurals, orally administered pain relievers and intravenously injected pain relievers, may significantly reduce the mother's ability to feel pain along with tactile sensation in the perianal tissues, the monitoring may take that into account to determine to increase the amount of pressure being applied by the perianal support device. This may assist with being able to have a tactile feel of the device on the patient. In other examples where the device is being primarily used for hemorrhoid prevention, this may be less of an issue (though still potentially useful).

At decision block 512, it is determined whether to change the position of the perianal support device 100, such as to either increase or decrease the amount of pressure/contact applied by the central support element 102 during childbirth labor.

If it is determined to not change the position, then method 500 returns to block 510 to continue monitoring. Monitoring may continue until it is determined to make a change, or when childbirth labor completes (at least delivery of the child, if not also the placenta). That is, where no change in position becomes requested or desired/necessary, then method 500 may proceed from block 510 to block 516.

If it is instead determined at decision block 512 to change the position of the perianal support device 100 on the patient, then the method 500 proceeds to block 514. At block 514, the user moves the perianal support device 100 to a second position. This may include the user grasping a gripping portion, such as gripping portion 116, detaching it from the corresponding anchor pad such that the anchor pad remains in place on the patient's buttock, and using at least the gripping portion 116 to place the distal portion 112 over another region of the anchor pad to achieve a desired amount of pressure. This may be repeated with the other gripping portion 118 for the distal portion 114 over another region of the other anchor pad to achieve the desired amount of pressure (whether increasing or decreasing the pressure).

In some examples, the actions from blocks 510, 512, and 514 may occur in approximate synchronization with the patient's contractions. Thus, the user may gradually increase the pressure applied by the perianal support device 100 in sync with the increase in intrauterine pressure due to contractions. In other instances, the user may decrease the pressure applied by the perianal support device 100 in sync with the increase in intrauterine pressure due to contractions, particularly if labor is progressing as desired and/or to protect against hemorrhoids or other issues as pressure increases during contractions.

Method 500 may return to block 510 to again monitor and repeat the actions above whenever it is determined to make another change. Otherwise, the method 500 may proceed to block 516. At block 516, the user removes the perianal support device 100 upon completion of childbirth labor, whether just after the delivery of the child, or also after the delivery of the placenta. This is accomplished by respectively grabbing the gripping portions of each compression element and lifting the compression elements from the anchoring points (either against respective anchor pads or the crown regions of the buttocks themselves, when no anchor pads are used). Where used, the anchor pads may be removed as well.

Figure 6:
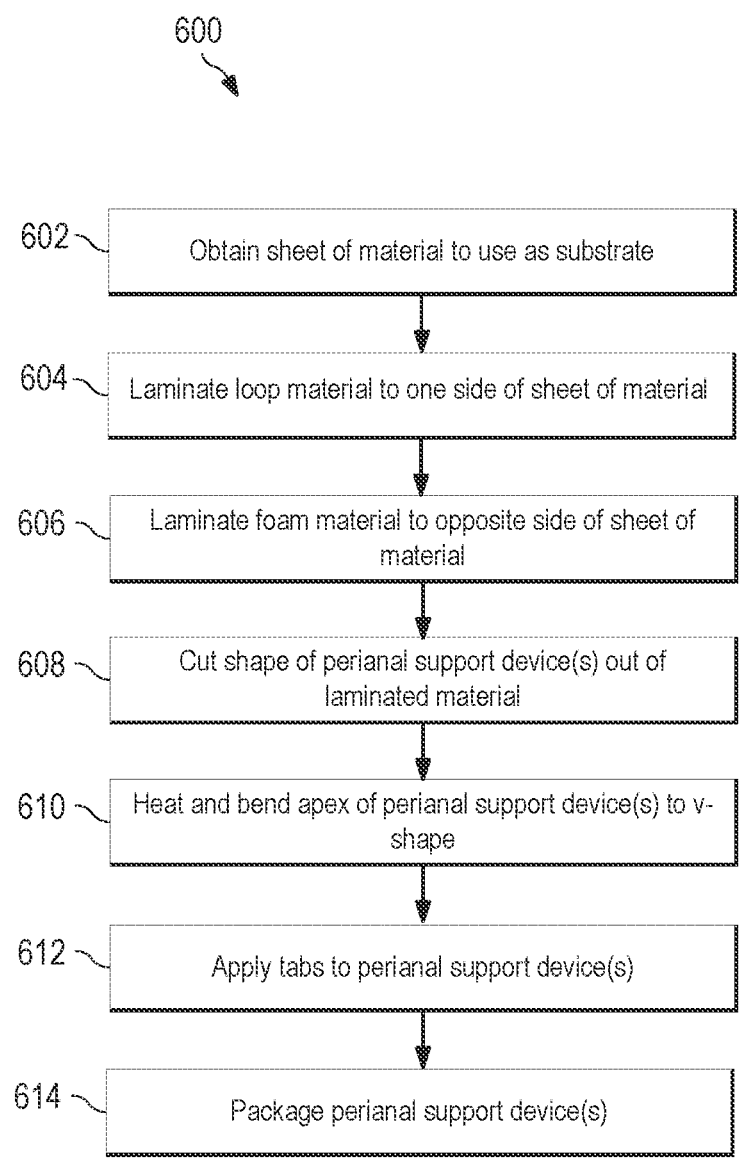
FIG. 6 is a flow chart illustrating a method of manufacturing a perianal support device according to aspects of the present disclosure.

Turning now to FIG. 6, a method 600 is illustrated in a flow chart of manufacturing a perianal support device 100 according to some aspects of the present disclosure. It is understood that additional steps can be provided before, during, and after the steps of the method 600, and that some of the steps described can be replaced or eliminated for other embodiments of the method 600. For example, in examples where the perianal support device 100 is manufactured via an injection molding process, at least blocks 602 and 610 below may be omitted. In such examples, the substrate (layer 152 of FIG. 1C) may be injection molded (e.g., to substantially its v-shaped form at the apex to the flex regions) and then the laminating of blocks 604/606 may be performed. For example, where molded, the perianal support device 100 may be formed by compression molding, transfer molding, reactive injection molding, extrusion, blow molding, casting, heat-forming, machining, deforming a sheet, bonding, joining or combinations thereof. In other embodiments, suitable materials for perianal support device 100 include polymers, metals, ceramics or combinations thereof. The materials can be or include alone or in combination: hard solids, soft solids, tacky solids, viscous fluid, porous material, woven fabric, braided constructions, or non-woven mesh. Examples of polymers include polyethylene, polyester, Nylon, Teflon, polyproplylene, polycarbonate, acrylic, PVC, styrene, PEEK, etc. Examples of ceramics include alumina, zirconia, carbon, carbon fibers, graphites, etc. Examples of suitable metals include titanium, stainless steel, cobalt-chrome, etc. Discussion below will describe aspects of manufacturing the device from a sheet of material, with the exceptions noted above when injection molded instead.

At block 602, a sheet of a material suitable for use as layer 152 (FIG. 1C) is obtained. This may be a thin sheet of polycarbonate (e.g., medical grade), for example, such as having a thickness on the order of between 20 thousandths and 50 thousandths of an inch, or 25 thousandths to 35 thousandths of an inch (e.g., 30 thousandths of an inch). In some embodiments, the sheet may have a uniform thickness across its width and length, while in other examples it may vary from thicker in some regions than others. For example, thicker regions may correspond to those regions that will be used subsequently to form central support elements 102 of one or more perianal support devices 100. Examples of other materials for the sheet may include other polymers (e.g., include polyethylene, polyester, Nylon, Teflon, polypropylene, acrylic, PVC, styrene, PEEK, etc.), ceramics (e.g., alumina, zirconia, carbon, carbon fibers, graphites, etc.), or metals (e.g., titanium, stainless steel, cobalt-chrome, etc.).

At block 604, a loop material is adhered to one side of the sheet of material from block 602. For example, an adhesive may be used to laminate the loop material as first layer 150 to the second layer 152 (see FIG. 1C). This may be applied across the generally full width and length of the sheet of material. Alternatively, this may be applied to the sections of the sheet of material that will be used to subsequently form compression elements 104, 106 (e.g., leaving the sections that will become central support element 102 of each device without the loop material laminated to it). In yet further examples, the loop material may be laminated to squares that will form distal portions 112, 114 in the finished devices (e.g., to reduce on cost).

At block 606, a foam material is adhered to the other side of the sheet of material from block 602. For example, a foam such as EVA foam (medical grade) may be used. This may be laminated the foam as third layer 154 to the second layer 152 (FIG. 1C) using an adhesive, such as the same adhesive as was used at block 604 or a different type. The third layer 154 of EVA foam may be several times thicker than that of the sheet of material. Other examples of material that may be used as foam material include polyurethane, silicon, rubber, or cotton (to name a few examples). This may be applied across the generally full width and length of the sheet of material. Alternatively, this may be applied to the sections of the sheet of material that will be, in the finished device, more likely to be points of contact between a user or patient and the device. While described as occurring after block 604, the lamination of the loop material and the foam material may occur in the opposite order, at approximately the same time, etc., to optimize the manufacturing process. In other examples, block 604 may be omitted where a foam or other material is not adhered to the other side of the sheet of material.

At block 608, the laminated material, which includes first, second, and third layers (or first and second layers in some examples), is cut into the shape of the full perianal support device 100 (before bending). This may include a narrower central section, where central support element 102 is located, and wider (potentially bulbous) distal portions 112, 114 where the compression elements 104, 106 are located. In some examples, gripping portions 116, 118 are cut as part of block 608, while in other examples the gripping portions 116, 118 are formed separately (such as by taking two same-sized pieces of hook material and adhering their backs to each other, so that both sides of the gripping portion have hook material facing outwards). For example, the shape is die cut from the laminated material.

At block 610, the cut-outs of the laminated material are bent to shape, such as to a general v-shaped configuration. For example, the material may be bent so that an internal angle (375, FIG. 3) between the compression elements exists. For example, that angle may be between 30 and 140 degrees (e.g., approximately 90 degrees). This may include heating the material, at least in the locations where the central support elements 102 will be, and bending to achieve the desired angle while heated. Once heat treated in this manner, the perianal support devices 100 that result will substantially retain the v-shape once cooled (at least at the central support element 102—beyond the flex region 162, as noted previously, the compression elements 104, 106 bend to conform generally to the patient's anatomy when applied). In other examples, the bending may be performed to the desired angle without heat treating first.

At block 612, the gripping portions 116, 118 are applied to distal ends 120, 122 of the compression elements 104, 106 for each perianal support device 100. Where the gripping portions are included as integral parts of the perianal support devices 100, block 612 may be omitted. In other examples, block 612 is omitted in the sense that the gripping portions 116, 118 are die cut with the first material 150 and therefore remain with the compression elements 104, 106 once the first material 150 is laminated to the second material 152 (see block 604 above). In this example, therefore, the gripping portions 116, 118 may be integrally formed with the first material 150, but since the gripping portions 116, 118 extend beyond the distal ends 120, 122 of the compression elements 104, 106, the gripping portions 116, 118 may not be laminated to the second material 152 but instead be free and available for grasping as discussed elsewhere herein. Further, where it is desired for the gripping portions 116, 118 to not be pre-assembled as part of a kit, block 612 may be omitted.

At block 614, each perianal support device 100 is packaged. For example, each device is provided sterile in a package for later use on a patient. The devices may be packaged with gripping portions (whether pre-assembled or included separately) or may be packaged separately from them. Block 614 may include packaging anchor pads with the devices as well, to constitute a kit as discussed previously. In examples where the perianal support devices have adhesive instead of loop material, anchor pads might be omitted (or may still be included where the adhesive is configured to adhere to another specific type of material which is on a surface of each anchor pad).

Applicants note that the procedures disclosed herein are merely exemplary and that the systems and method disclosed herein may be utilized for numerous other medical processes and procedures. Although several selected implementations have been illustrated and described in detail, it will be understood that they are exemplary, and that a variety of substitutions and alterations are possible without departing from the spirit and scope of the present invention. For example, while gripping portions 116, 118 have been described herein as being useful, in some instances gripping portions 116, 118 may be omitted while other features of the invention described herein are maintained. Accordingly, the true scope of the invention is set forth in the following claims.

We claim:

1. A perianal support device, comprising:
a central support element comprising a continuous compression surface apex configured and dimensioned to extend across an anal orifice of a patient in a sagittal plane of the patient;
a first compression element extending from the central support element in a first lateral direction, the first compression element comprising a first resilient, flexible member configured to follow a first contour of a first buttock of the patient, the first compression element further comprising a first surface comprising a first loop portion of a hook and loop fastener facing the first buttock of the patient, and a second surface comprising a soft material facing away from the first buttock,
wherein the first loop portion is configured to releasably attach to a first hook portion of a hook and loop fastener of a first anchor pad adapted to be releasably attached across a first crown of the first buttock;
a second compression element extending from the central support element in a second lateral direction opposite the first lateral direction, the second compression element comprising a second resilient, flexible member configured to follow a second contour of a second buttock of the patient, the second compression element further comprising a third surface comprising a second loop portion of a hook and loop fastener facing the second buttock of the patient, and a fourth surface comprising a soft material facing away from the second buttock,
wherein the second loop portion is configured to releasably attach to a second hook portion of a hook and loop fastener of a second anchor pad adapted to be releasably attached across a second crown of the second buttock;
a first tab comprising a third hook portion of a hook and loop fastener configured to releasably attach to the first loop portion of the first surface at a first distal end of the first compression element; and a second tab comprising a fourth hook portion of a hook and loop fastener configured to releasably attach to the second loop portion of the third surface at a second distal end of the second compression element, wherein the first tab is configured for gripping to manually attach the first surface to the first anchor pad and the second tab is configured for gripping to manually attach the third surface to the second anchor pad.

2. The perianal support device of claim 1, wherein the first and second resilient, flexible members comprise a thin plastic substrate.

3. The perianal support device of claim 2, wherein the thin plastic substrate comprises a common substrate extending continuously from the first distal end of the first compression element, across the central support element, to the second distal end of the second compression element.

4. The perianal support device of claim 2, wherein the thin plastic substrate comprises a thickness of between 25 thousandths of an inch and 35 thousandths of an inch and is formed from a medical grade polycarbonate material.

5. The perianal support device of claim 1, wherein the first and second compression elements comprise a first width adjacent to the central support element and a second width proximate to the first and second distal ends of the respective first and second compression elements, the first width being less than the second width.

6. The perianal support device of claim 1, wherein the first and second anchor pads comprise respective adhesive segments configured to adhere at least a portion of the first and second anchor pads to skin of the first and second crowns, respectively.

7. The perianal support device of claim 1, wherein the central support element is connected to the first compression element via a first flex region at a proximal end of the first compression element, and to the second compression element via a second flex region at a proximal end of the second compression element.

8. The perianal support device of claim 1, wherein the first and second tabs comprise a length and width smaller than a length of the continuous compression surface apex of the central support element.

9. The perianal support device of claim 1, wherein the soft material of each of the second surface and the fourth surface comprises a medical grade foam.

10. A perianal support device for use on a patient, comprising:
a central support element comprising a continuous compression surface apex configured and dimensioned to extend across an anal orifice of the patient in a sagittal plane of the patient;
a first compression element comprising a first resilient, flexible member configured to follow a first contour of a first buttock of the patient and a first surface adapted to face the first buttock of the patient, the first surface having a first lateral extent configured to releasably attach to a first anchor pad placed across a first crown of the first buttock, the first compression element further comprising a first tab extending outwardly laterally from said first compression element, said first tab having a first lateral tab extent less than the first lateral extent; and
a second compression element comprising a second resilient, flexible member configured to follow a second contour of a second buttock of the patient and a second surface adapted to face the second buttock of the patient, the second surface having a second lateral extent configured to releasably attach to a second anchor pad placed across a second crown of the second buttock, the second compression element further comprising a second tab extending outwardly from said second compression element, said second tab having a second lateral extent less than the second lateral extent,
wherein the first and second tabs are configured for gripping to manually attach the first and second surfaces to the first and second anchor pads, respectively.

11. The perianal support device of claim 10, wherein:
the first and second surfaces comprise a loop portion of a hook and loop fastener,
the first and second anchor pads comprise a hook portion of the hook and loop fastener, and
the first and second surfaces are configured to releasably attach to the first and second anchor pads, respectively, using the hook and loop fastener.

12. The perianal support device of claim 10, wherein the first and second anchor pads comprise respective adhesive segments configured to adhere at least a portion of the first and second anchor pads to skin of the first and second crowns, respectively.

13. The perianal support device of claim 10, wherein the first and second resilient, flexible members comprise a thin plastic substrate.

14. The perianal support device of claim 13, wherein the thin plastic substrate comprises a common substrate extending continuously from a first distal end of the first compression element, across the central support element, to a second distal end of the second compression element.

15. The perianal support device of claim 13, wherein the thin plastic substrate comprises a thickness of between 25 thousandths of an inch and 35 thousandths of an inch and is formed from a medical grade polycarbonate material.

16. The perianal support device of claim 10, wherein the first and second compression elements comprise a first width adjacent to the central support element and a second width proximate to first and second distal ends of the respective first and second compression elements, the first width being less than the second width, a peripheral extent of each of the first and second compression elements being curved.

17. The perianal support device of claim 10, wherein the central support element is connected to the first compression element via a first flex region at a proximal end of the first compression element, and to the second compression element via a second flex region at a proximal end of the second compression element.

18. The perianal support device of claim 10, wherein:
the first tab is releasably engaged to the first compression element at a distal end of the first compression element, and
the second tab is releasably engaged to the second compression element at a distal end of the second compression element.

19. A perianal support device for use on a patient, comprising:
a central contact surface configured and dimensioned to extend across an anal orifice of the patient in a sagittal plane of the patient from an anterior portion posterior to a vaginal opening of the patient to a posterior portion posterior to the anal orifice of the patient;
a first compression element extending from the central contact surface in a first lateral direction, the first compression element comprising a first surface configured to follow a first contour of a first buttock of the patient within a gluteal cleft of the patient, and releasably attach to a first anchor pad that is adapted to be placed across a first crown of the first buttock; and a second compression element extending from the central contact surface in a second lateral direction, the second compression element comprising a second surface configured to follow a second contour of a second buttock of the patient within the gluteal cleft of the patient, and releasably attach to a second anchor pad that is adapted to be placed across a second crown of the second buttock, wherein the perianal support device comprises a resilient, flexible member comprising a thin plastic substrate extending continuously from a first distal end of the first compression element, across the central support element, to a second distal end of the second compression element, the first surface and the second surface being disposed on one side of the thin plastic substrate separated by the central contact surface, and a medical grade foam being disposed on an opposite side of the thin plastic substrate continuously from the first distal end of the first compression element, across the central support element to the second distal end of the second compression element.

20. The perianal support device of claim 19, further comprising a first tab extending from the first compression element and a second tab extending from the second compression element, the first and second tabs configured for gripping to manually attach the first and second surfaces to the first and second anchor pads, respectively.

* * * * *